US008470861B2

(12) United States Patent
Anders et al.

(10) Patent No.: US 8,470,861 B2
(45) Date of Patent: Jun. 25, 2013

(54) MITOCHONDRIA-TARGETED ANTIOXIDANT PRODRUGS AND METHODS OF USE

(75) Inventors: Marion W. Anders, Pittsford, NY (US); James L. Robotham, Seattle, WA (US); Shey-Shing Sheu, Pittsford, NY (US); Paul Spencer Brookes, Rochester, NY (US); Jalil Shojaie, Rochester, NY (US); Leif Olson, Riverside, RI (US); Richard L. Parton, Webster, NY (US)

(73) Assignee: University of Rochester, Rochester, NY (US)

( * ) Notice: Subject to any disclaimer, the term of this patent is extended or adjusted under 35 U.S.C. 154(b) by 511 days.

(21) Appl. No.: 12/694,337

(22) Filed: Jan. 27, 2010

(65) Prior Publication Data

US 2010/0168198 A1 Jul. 1, 2010

Related U.S. Application Data

(63) Continuation-in-part of application No. 12/094,618, filed as application No. PCT/US2006/061081 on Nov. 20, 2006, now abandoned.

(60) Provisional application No. 60/739,033, filed on Nov. 22, 2005.

(51) Int. Cl.
| | |
|---|---|
| *A01N 43/50* | (2006.01) |
| *A01N 43/32* | (2006.01) |
| *A01N 43/26* | (2006.01) |
| *A01N 43/16* | (2006.01) |
| *A01N 31/14* | (2006.01) |
| *A61K 31/415* | (2006.01) |
| *A61K 31/385* | (2006.01) |
| *A61K 31/35* | (2006.01) |
| *A61K 31/075* | (2006.01) |
| *A61K 31/08* | (2006.01) |
| *C07D 339/00* | (2006.01) |
| *C07D 339/02* | (2006.01) |
| *C07D 341/00* | (2006.01) |
| *C07D 409/00* | (2006.01) |
| *C07D 239/00* | (2006.01) |
| *C07D 239/02* | (2006.01) |

(52) U.S. Cl.
USPC ........... 514/385; 514/436; 514/440; 514/456; 514/720; 514/722; 549/20; 549/35; 544/242

(58) Field of Classification Search
USPC .... 514/385, 456, 720, 722, 436, 440; 549/20, 549/35; 544/242
See application file for complete search history.

(56) References Cited

U.S. PATENT DOCUMENTS

| | | | | |
|---|---|---|---|---|
| 4,036,970 | A | * | 7/1977 | Walker et al. ................. 514/399 |
| 4,642,132 | A | * | 2/1987 | Schirmer et al. .............. 504/225 |
| 6,245,811 | B1 | | 6/2001 | Horrobin et al. .............. 514/547 |
| 6,770,672 | B1 | | 8/2004 | Sanders et al. ................ 514/458 |
| 2002/0048798 | A1 | * | 4/2002 | Avery et al. ................... 435/183 |
| 2005/0165101 | A1 | | 7/2005 | Gandhi ......................... 514/548 |

FOREIGN PATENT DOCUMENTS

JP 57059871 A * 4/1982

OTHER PUBLICATIONS

Parang et al. "Synthesis and Antifungal Activities of Myristic Acid Analogs" Arch. Pharm. Pharm. Med. Chem., 1996, vol. 329, pp. 475-482.*
Kajimoto et al. "Transmission of Substituent Effects through Oxygen and Sulfur Atoms. II. The Ionization Equilibirium Constants of Ring-substituted cis-beta-Phenoxyacrylic Acids" bulletin of the Chemical Society of Japan, 1973, vol. 46, pp. 1425-1428.*
Macchia et al. "Synthesis, Antiinflammatory activity and Platelet Anti-Aggregating Activity of a New Series of beta-aminopropionic acids" II Farmaco, 1995, vol. 50(2), pp. 83-90.*
Persson et al. "Rational design and synthesis of new quorum-sensing inhibitors derived from acylated homoserine lactones and natrual products from garlic" Org. Biomol. Chem., 2005, vol. 3, pp. 253-262.*
Jones et al. "(1,3-dithiolan-2-yl)acetonitrile. Versatile three-carbon building block" Synthetic Communications, 1974, vol. 4(6), pp. 331-334.*
Bell, H. K. and Duewell, H. "Synthesis of Some Linear Benzochromanones" Aust. J. Chem. 1962 vol. 16 (1): 101-106.
Fan et al. "DABCO-Catalyzed Reaction of Phenols of 1,2-Diphenols with Activated Alkynes Leading to the Formation of Alkenoic Acid Esters of 1,3-Dioxole Derivatives" Synthesis 2006 vol. 14: 2286-2292.
Filipovska et al. "Synthesis and Characterization of a Triphenylphosphonium-conjugated Peroxidase Mimetic" Journal of Biological Chemistry 2005 vol. 280 (25): 24113-24126.
Fitzsimmons et al. "Medium-Chain Acyl-CoA Dehydrogenase- and Enoyl-CoA Hydratase-Dependent Bioactivation of 5,6-Dichloro-4-thia-5-hexenoyl-CoA" Biochemistry 1995 vol. 34: 4276-4286.
Fromenty et al. "Tianeptine, A New Tricyclic Antidepressant Metabolized by β-Oxidation of its Heptanoic Side Chain, Inhibits the Mitochondrial Oxidation of Medium and Short Chain Fatty Acids in Mice" Biochemical Pharmacology 1989 vol. 38 (21): 3743-3751.
Kelso et al. "Selective Targeting of a Redox-active Ubiquinone to Mitochondria within Cells" The Journal of Biological Chemistry 2001 vol. 276 (7): 4588-4596.
Mao et al. "Mitochondrial β-Oxidation of 2-Methyl Fatty Acids in Rat Liver" Archives of Biochemistry and Biophysics 1995 vol. 321 (1): 221-228.
Lau et al. "The Reductive Half-Reaction in Acyl-CoA Dehydrogenase from Pig Kidney: Studies with Thiaoctanoyl-CoA and Oxaoctanoyl-CoA Analogues" Biochemistry 1988 vol. 27: 5089-5095.

(Continued)

*Primary Examiner* — Kendra D Carter
(74) *Attorney, Agent, or Firm* — Licata & Tyrrell P.C.

(57) ABSTRACT

The present invention is a mitochondria-targeted antioxidant prodrug useful for the prevention or treatment of diseases or conditions associated with mitochondrial dysfunction resulting from changes in the mitochondrial redox environment. Antioxidant prodrugs of the invention are produced by modifying an antioxidant to a fatty acid so that the resulting prodrug is targeted to and activated by an enzyme of mitochondrial fatty acid beta-oxidation.

4 Claims, 2 Drawing Sheets

OTHER PUBLICATIONS

Muratovska et al. "Targeting Large Molecules to Mitochondria" Advanced Drug Delivery Reviews 2001 vol. 49: 189-198.

Murphy et al. "Superoxide Activates Uncoupling Proteins by Generating Carbon-centered Radicals and Initiating Lipid Peroxidation" The Journal of Biological Chemistry 2003 vol. 278 (49): 48534-48545.

Sheu et al. "Targeting Antioxidants to Mitochondria: A New Therapeutic Direction" Biochemicia et Biophysica Acta 2006 vol. 1762: 256-265.

Smith et al. "Delivery of Bioactive Molecules to Mitochondria in Vivo" PNAS 2003 vol. 100 (9): 5407-5412.

Smith et al. "Selective Targeting of an Antioxidant to Mitochondria" European Journal of Biochemistry 1999 vol. 263: 709-716.

Stonard, M. D. "Further Studies on the Site and Mechanism of Action of S-(1,2 Dichlorovinyl)-$_L$-Cysteine and S-(1,2 Dichlorovinyl)-3-Mercaptopropionic Acid in Rat Liver" Biochemical Pharmacology 1973 vol. 22: 1329-1335.

Stonard, M. D. and Parker, V. H. "2-Oxoacid Dehydrogenases of Rat Liver Mitochondria as the Site of Action of S-(1,2 Dichlorovinyl)-$_L$-Cysteine and S-(1,2, Dichlorovinyl)-3-Mercaptopropionic Acid" Biochemical Pharmacology 1971 vol. 20: 2417-2427.

Tweit et al. "Synthesis of Antimicrobial Nitroimidazolyl 2-Sulfides, -Sulfoxides, and -Sulfones" Journal of Medicinal Chemistry 1973 vol. 16 (10): 1161-1169.

Weissig et al. "Targeting of Low-Molecular Weight Drugs to Mammalian Mitochondria" Drug Design Reviews—Online 2004 vol. 1: 15-28.

Weissig, V. "Mitochondrial-Targeted Drug and DNA Delivery" Critical Reviews in Therapeutic Drug Carrier Systems 2003 vol. 20 (1): 1-62.

* cited by examiner

MITOCHONDRIA-TARGETED ANTIOXIDANT PRODRUGS AND METHODS OF USE

This application is a continuation-in-part application of U.S. Ser. No. 12/094,618 filed Sep. 11, 2008; which is the national phase of PCT/US2006/061081 filed Nov. 20, 2006 which claims priority to U.S. Provisional No. 60/739,033 filed Nov. 22, 2005.

BACKGROUND OF THE INVENTION

Physiologically, mitochondria perform a variety of key cellular regulatory processes, including ATP production, intracellular $Ca^{2+}$ regulation, reactive oxygen species (ROS) generation and detoxication, and apoptosis (Tzagoloff (1982) Mitochondria, Plenum Press, New York). Mitochondria use approximately 90% of the consumed $O_2$ for oxidative phosphorylation and ATP synthesis. Thus, the proteins involved in the mitochondrial electron transport chain are probable sites for ROS generation. Intracellular glutathione, glutathione peroxidase, glutathione transferases, catalase, superoxide dismutase, and a variety of other antioxidant defenses keep ROS concentrations in check, which allows cells to function homeostatically thereby preventing oxidative stress (Abid, et al. (2004) *J. Biol. Chem.* 279:44030-44038; Zhang, et al. (2002) *J. Virol.* 76:355-363; Li, et al. (2000) *Cancer Res.* 60:3927-3939; Warner, et al. (1996) *Am. J. Physiol.* 271: L150-L158; Schiavone & Hassan (1988) *J. Biol. Chem.* 263: 4269-4273). A shift in the balance between ROS generation and destruction to overproduction or decreased detoxication is associated with chronic diseases (Ross, et al. (1997) *Am. J. Kidney Dis.* 30:489-494).

The etiology of a range of diseases is associated with the generation of excess reactive oxygen species. Steady-state maintenance of ROS/antioxidant ratio is, however, essential for cell signaling. Reactive oxygen species generated in cells include the superoxide anion radical ($O_2^{\cdot-}$), hydrogen peroxide ($H_2O_2$), hypochlorous acid (HOCl), hydroxyl radical (OH$^{\cdot}$), and singlet oxygen ($^1O_2$). These ROS are formed as a consequence of endogenous enzymatic and nonenzymatic reactions within the cell and within mitochondria. ROS may also be formed in response to external stimuli and chemicals.

ROS are generated by normal biochemical reactions in the cell. Leakage of electrons from the mitochondrial electron transport chain is a significant source of mitochondrial ROS, particularly superoxide (Boveris & Cadenas (1997) In: Oxygen, Gene Expression, and Cellular Function, Clerch & Massaro, eds., Marcel Dekker, New York, pp. 1-25). Moreover, the TCA cycle enzymes α-ketoglutarate dehydrogenase and the pyruvate dehydrogenase complex also generate superoxide and $H_2O_2$ (Starkov, et al. (2004) J. Neurosci. 24:7779-7788). Superoxide is also generated by NADPH oxidase, which is found in phagocytic and nonphagocytic macrophages (Quinn & Gauss (2004) *J. Leukoc. Biol.* 76:760-781), and by xanthine dehydrogenase/oxidase (Rajagopalan (1997) In: Biotransformation, Guengerich, ed., Elsevier, New York pp. 165-178). Hydrogen peroxide is produced by mitochondrial monoamine oxidase (Cashman (1997) In: Biotransformation supra pp. 69-96) and by the superoxide dismutase (MnSOD and Cu/ZnSOD)-catalyzed dismutation of superoxide (Fridovich (1995) *Annu. Rev. Biochem.* 64:97-112). In addition, peroxisomal acyl-CoA oxidases also generate hydrogen peroxide (Reubsaet, et al. (1988) *Biochim. Biophys. Acta* 958:434-442). The myeloperoxidase-catalyzed generation of hypochlorous acid is an important line of defense against invading microorganisms (Winterbourn, et al. (2000) *Curr. Opin. Hematol.* 7:53-58).

There is no known enzymatic route to detoxify the hydroxyl radical, which may be produced by the Haber-Weiss reaction in the presence of transition metals, particularly iron. Singlet oxygen may be formed by photodynamic processes or from the reaction of hypochlorous acid with hydrogen peroxide.

Reactive nitrogen species have also been implicated in cell damage and death. Nitric oxide synthase catalyzes the synthesis of the radical species nitric oxide (NO$^{\cdot}$), which may react with superoxide to give peroxynitrite (ONOO$^-$). ROS generation may also be associated with external stimuli. UV and high-energy irradiation, the metabolism of some xenobiotics, air pollutants ($O_3$), and the redox cycling of quinones and nitroaromatics are all associated with ROS generation.

The balance between these sources of ROS depends on the physiologic and pathophysiologic states of the organism, and it is often difficult to pinpoint the source of ROS generation. It is, however, known that ROS exert important regulatory functions (Dröge (2002) *Physiol. Rev.* 82:47-95). Hence, a basal or tonal concentration of ROS, especially at the level of the mitochondrion, is essential for basic cell signaling processes. In other words, all ROS are not created equal, and compartmentalization and concentration gradients are highly important. Abolishment of all cellular ROS by vigorous use of antioxidants may not be beneficial and, indeed, may prove harmful. The requirement for a basal ROS tone may explain why many antioxidant-based therapies have failed.

Mitochondria are attractive targets for drug-delivery strategies because of their roles in cellular energy metabolism, programmed (apoptotic) cell death, calcium homeostasis, and cell signaling. Moreover, mutations in mitochondrial DNA are associated with a range of human diseases, again making mitochondria attractive targets for mitochondrial gene therapy. Hence, strategies have been developed to target small and large molecules with therapeutic potential to mitochondria (Muratovska, et al. (2001) *Adv. Drug Deliv. Rev.* 49:189-198; Weissig (2003) *Crit. Rev. Ther. Drug Carrier Syst.* 20:1-62; Weissig, et al. (2004) *Drug Design Rev.-Online* 1:15-28).

For example, the high potential gradient across the mitochondrial inner membrane can be exploited to deliver lipophilic cations to mitochondria. Cationic compounds, such as rhodamine 123 and tetraphenylphosphonium (TPP$^+$), have been adopted for mitochondrial membrane potential determinations and a series of cationic antioxidants that preferentially accumulate in mitochondria have been developed (Ross, et al. (2005) *Biochemistry* (Moscow) 70:222-230). Further, a triphenylphosphonium-based, mitochondria-targeted mixture of ubiquinol (mitoquinol) and ubiquinone (mitoquinone), i.e., MitoQ (Kelso, et al. (2001) *J. Biol. Chem.* 276:4588-459), as well as MitoVit E (Smith, et al. (1999) *Eur. J. Biochem.* 263:709-716); MitoPBN (Murphy, et al. (2003) *J. Biol. Chem.* 278:48534-48545); MitoPeroxidase, a mitochondria-targeted analog of ebselen (Filipovska, (2005) *J. Biol. Chem.* 280:24113-24126); and glutathione choline ester (MitoGSH) and N-acetyl-L-cysteine choline ester (MitoNAC) have been synthesized for delivery of an antioxidant to mitochondria to selectively prevent mitochondrial oxidative damage.

SUMMARY OF THE INVENTION

The present invention is a mitochondria-targeted antioxidant prodrug composed of a selected, fatty acid-modified antioxidant which is activated by an enzyme of mitochondrial fatty acid beta-oxidation. In particular embodiments, the antioxidant prodrug is in admixture with a pharmaceutically acceptable carrier to form a pharmaceutical composition.

The present invention is also a method for producing a mitochondria-targeted antioxidant prodrug by modifying a selected antioxidant to a fatty acid to produce a mitochondria-targeted antioxidant prodrug which is activated by an enzyme of mitochondrial fatty acid beta-oxidation.

Use of the mitochondria-targeted antioxidant prodrug in methods for decreasing mitochondrial dysfunction resulting from changes in the mitochondrial redox environment and preventing or treating a disease associated with mitochondrial dysfunction is also provided.

DETAILED DESCRIPTION OF THE INVENTION

Figure 1:
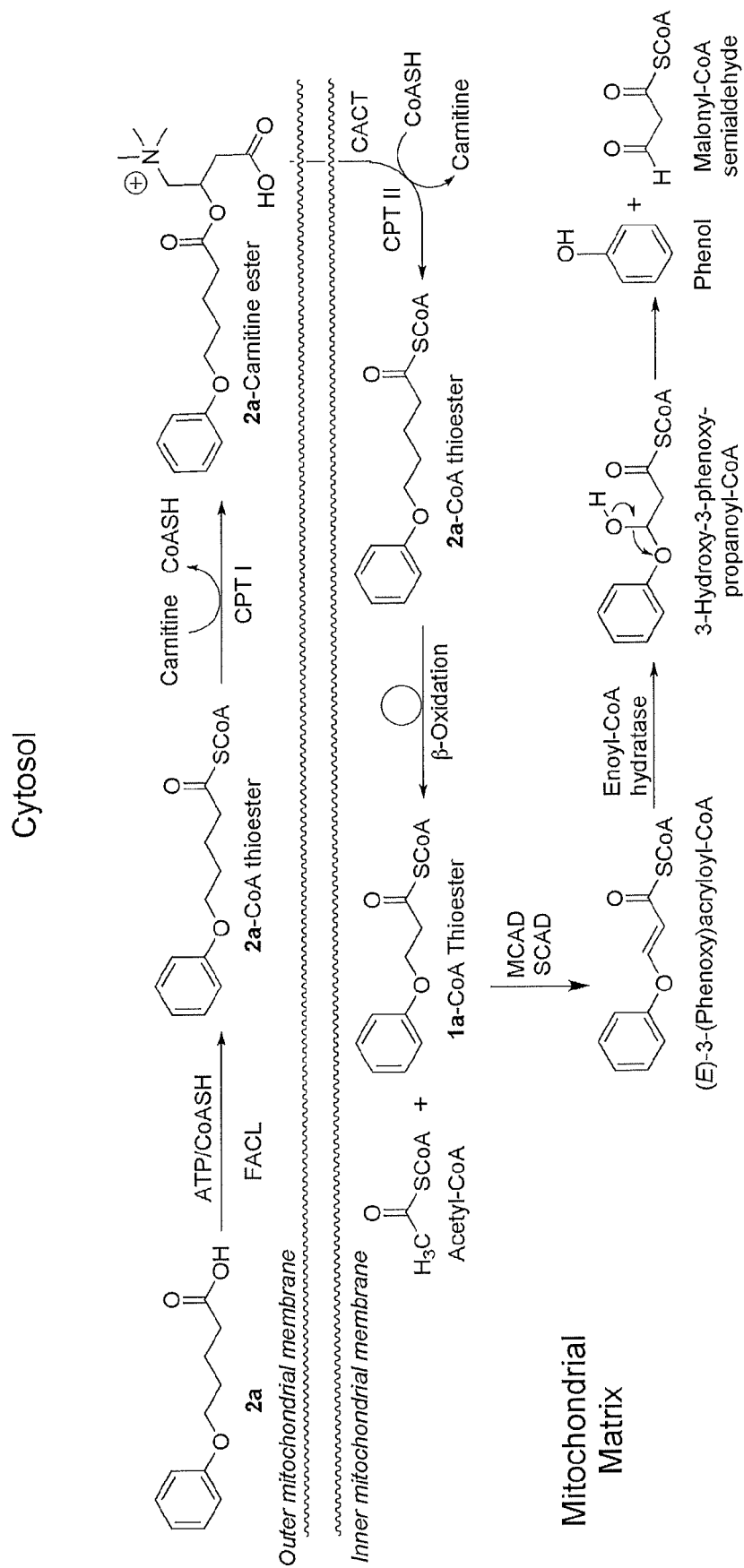
FIG. 1 depicts mitochondrial biotransformation of ω-(phenoxy)alkanoic acids. FACL, fatty-acid-CoA ligase; CPT-I, carnitine palmitoyltransferase-I; CACT, carnitine-acyl carnitine translocase; CPT-II, carnitine palmitoyltransferase-II; MCAD, medium-chain acyl-CoA dehydrogenase; SCAD, short-chain acyl-CoA dehydrogenase.

The present invention features antioxidant prodrugs that are specifically targeted to the mitochondria. The prodrug antioxidants of the instant invention can advantageously be used in the prevention and treatment of diseases associated with mitochondrial dysfunction resulting from changes in the mitochondrial redox environment because the instant prodrugs primarily exert their effects upon the mitochondria but may also exert their effects in other compartments of the cell.

As used in the context of the present invention, a prodrug is a compound that undergoes biotransformation via a metabolic process before exhibiting its pharmacological effects. Prodrugs are generally viewed as drugs containing specialized non-toxic protective groups used in a transient manner to alter or to eliminate undesirable properties in the parent molecule until the target site is reached. In accordance with the instant invention, an antioxidant prodrug is said to be targeted to the mitochondria by virtue of the unique mitochondrial localization of fatty acid β-oxidation enzymes that activate or release the antioxidant from its prodrug form within the mitochondria.

The term antioxidant, as used in the context of the instant invention, refers to a compound that, when present at low concentrations compared to those of an oxidizable substrate, significantly delays or prevents oxidation of that substrate. There is an abundance of oxidizable substrates in the cell, including proteins, lipids, carbohydrates, and DNA. Thus, antioxidants can function to prevent the formation of or to detoxify free radicals, to scavenge ROS (e.g., superoxide, hydrogen peroxide, hypochlorous acid, ozone, singlet oxygen, hydroxyl radical, and peroxyl, alkoxyl, and hydroperoxyl radicals) or their precursors.

Particular embodiments of the instant invention embrace a selected antioxidant compound, wherein a selected antioxidant is defined as an antioxidant containing a suitable group which can be modified to a fatty acid such that the modified antioxidant serves as a substrate of, and is activated by, an enzyme of fatty acid β-oxidation. In this respect, particular embodiments embrace compositions containing phenolic-, hydroxyl-, and thiol-based antioxidants modified to a fatty acid.

Suitable selected antioxidants with phenolic groups include chain-breaking phenol- and pyridinol-based antioxidants such as Vitamin E compounds including, for example, tocopherol (e.g., alpha-tocopherol, beta-tocopherol, gamma-tocopherol, delta-tocopherol), tocoquinone, tocotrienol (e.g., alpha-tocotrienol, beta-tocotrienol, gamma-tocotrienol, delta-tocotrienol), and analogues of Vitamin E such as TROLOX®, a compound which is more hydrosoluble than natural forms of Vitamin E; synthetic antioxidants such as 2,6-dimethyl-4-methoxyphenols (see, e.g., U.S. Pat. No. 4,552,682) and 6-amino-3-pyridinols (see, e.g., Wijtmans, et al. (2003) *Angewandte Chemie* 115:4506-4509), and exemplary compounds described herein.

Selected antioxidants with suitable hydroxyl groups include, but are not limited to, hydroxylamines such as N-substituted hydroxylamines including N-alkylhydroxylamines (e.g., N-tert-butylhydroxylamine, N-methylhydroxylamine); benzylhydroxylamines; and the like. Other suitable antioxidants include analogs of α-phenyl-N-tert-butylnitrone that contain a hydroxyl group.

Exemplary antioxidants with available thiol groups include, but are not limited to, thiol-based 4-mercaptoimidazole antioxidants such as 1,5-dimethyl-4-mercaptoimidazole and 2-Mercapto-1-methylimidazole (methimazole); dithiols such as 1,2-dithiol-3-thiones (e.g., 5-[p-methoxyphenyl]-3H-1,2-dithiol-3-thione, 4-methyl-5-pyrazinyl-3H-1,2-dithiole-3-thione), ethane-1,2-dithiol and propane-1,3-dithiol; and the like. See, e.g., 4-mercaptoimidazoles disclosed in U.S. Pat. No. 6,056,965 and Spaltenstein, et al. (1987) *J. Org. Chem.* 52:2977-79.

As used herein, an antioxidant prodrug based upon a particular fatty acid is intended to mean that the fatty acid is used to deliver the specified antioxidant to the mitochondria. For example, 5-aryloxypentanoic acids, which after one cycle of beta-oxidation yield 3-aryloxypropanoic acids, can effectively be used to deliver an antioxidant. Encompassed within the scope of the present invention are aryloxyalkanoic acids with a variety of fatty acid chain lengths and heteroatom positions. Moreover, ester, amide, alcohol and other functional derivatives of an aryloxyalkanoic acid are contemplated. As exemplified herein, a chain lengthened 3-(2,2,5,7,8-pentamethylchroman-6-yl)propanoic acid, synthesized according to the general method disclosed in U.S. Pat. No. 6,770,672, can be employed wherein upon beta-oxidation 2,2,5,7,8-pentamethylchroman-6-ol is produced. An exemplary fatty acid modification embraced by the present invention is an aryloxyalkanoic acid-based prodrug of a phenol- or pyridinol-based antioxidant, and chain lengthened analogs thereof.

Preparation of 3-(imidazol-4-ylthio)propanoic acid-based prodrugs of 4-mercaptoimidazole-based antioxidants can be carried out as exemplified herein by reacting a 4-mercaptoimidazole such as 1,5-dimethyl-4-mercaptoimidazole with an ethyl acrylate or ethyl 3-bromopropanoate, which after hydrolysis, affords the 4-mercaptoimidazole-based antioxidant prodrug. Similarly, the preparation of 3-(imidazol-2-ylthio)alkanoic acids can be carried out by reacting a 2-mercaptoimidazole such as methimazole with an ethyl acrylate or ethyl 3-bromopropanoate, which after hydrolysis affords the 2-mercaptoimidazole-based antioxidant prodrug. Furthermore, the preparation of 3-(imidazol-4-ylthio)acrylic acid- and 3-(imidazol-2-ylthio)acrylic acid-based prodrugs can be carried out with 4-mercaptoimidazoles, such as 1,5-dimethyl-4-mercaptoimidazole, or with 2-mercaptoimidazoles, such as methimazole, by reacting the 4- or 2-mercaptoimidazole with ethyl propiolate or propiolic acid; with ethyl propiolate, the resulting acrylate ester can be hydrolyzed to afford the 3-(imidazol-4-ylthio)acrylic acid- and 3-(imidazol-2-ylthio)acrylic acid-based antioxidant prodrugs.

Alternatively, thiol-based antioxidants such as the dithiol antioxidants can be readily modified by cleaving dimethylacetal and reacting the resulting aldehyde with the diothiol antioxidant so that subsequent hydrolysis affords the desired dithiol-based prodrug.

Further embraced by the present invention is a 3-aminoxypropanoic acid-based prodrug of a hydroxylamine. As exemplified herein, a hydroxylamine antioxidant such as an N-substituted hydroxylamine can be modified to yield its 3-aminoxypropanoic acid-based prodrug by Michael addition of the N-substituted hydroxylamine to acrylamide and subsequent hydrolysis.

Antioxidants for use in preparing the prodrugs of the present invention can be isolated from a natural source or wholly or partially synthetically- or recombinantly-produced. Methods for isolating or producing antioxidants or antioxidant extracts are well-established in the art, see, e.g., U.S. Pat. Nos. 6,770,672; 6,737,552; 6,660,320; 6,656,358; 6,653,530; 6,623,743; RE38,009; 6,429,356; 6,436,362; 6,262,279; 6,410,290; 6,231,853; and 5,714,362 and WO 91/04315.

In particular embodiments, the mitochondria-targeted antioxidant prodrug, as a composition of this invention, is selected from one or more of the following groups of compounds: a ω-(phenoxy)alkanoic acid; a 3-(phenoxy)acrylic acid; a ω-(1-methyl-1H-imidazol-2-ylthio)alkanoic acid; a ω-(1-methyl-1H-imidazol-2-ylthio)acrylic acid; a ω-(1,5-dimethylimidazol-4-ylthio)alkanoic acid; a ω-(1,5-dimethylimidazol-4-ylthio)acrylic acid; a N-alkyl 3-aminoxypropanoic acid; and a N-benzyl-3-aminoxypropanoic acid. In specific embodiments, the mitochondria-targeted antioxidant prodrug, as a composition of this invention, is selected from one or more of the following compounds: 3-(2,2,5,7,8-pentamethylchroman-6-yl)pentanoic acid; 3-(1,5-dimethyl-1H-imidazol-4-ythio)propanoic acid (compound 10); 2-(1,3-dithiolan-2-yl)acetic acid (compound 19); 2-(1,3-dithian-2-yl)acetic acid (compound 20); compound 26b; compound 26c; compound 26d; compound 28a; compound 29; compound 30a; and compound 30b. In yet other embodiments, a mitochondria-targeted antioxidant prodrug, as a composition of matter within the scope of this invention, does not include compounds 25a-25d, compound 26a, compound 27, or compound 28b.

While specific antioxidants and the preparation of prodrugs thereof are disclosed herein, such disclosure in no way limits the types antioxidants that could be modified to a fatty acid to serve as a substrate of, and be activated by, a fatty acid β-oxidation enzyme.

Mitochondria-targeted prodrugs of the present invention are activated by the fatty acid β-oxidation enzymatic machinery present in mitochondria. Advantageously, xenobiotic fatty acids, such as N-substituted 3-aminoxypropanoic acids and 3-aryloxypropanoic acids are short- or medium-chain fatty acids that enter mitochondria directly without the necessity for acyl carnitine formation and are converted to their acyl-CoA thioesters by ligases present in mitochondria (Vessey, et al. (1999) *Biochim. Biophys. Acta* 1428:455-462). Moreover, there are several examples of the biotransformation and bioactivation of xenobiotic fatty acids by mitochondria. S-(1,2-Dichlorovinyl)-3-mercaptopropionic acid is directly toxic to mitochondria without prior acyl-CoA or carnitine ester formation (Stonard (1973) *Biochem. Pharmacol.* 22:1329-1335; Stonard & Parker (1971) *Biochem. Pharmacol.* 20:2417-2427). This potent mitochondrial poison, as well as 5,6-dichloro-4-thia-5-hexenoic acid and related 5,6, 6-trihalo-4-thiahexanoic acids, undergo fatty acid β-oxidation-dependent bioactivation (Fitzsimmons, et al. (1995) *Biochemistry* 34:4276-4286). Moreover, the fatty acid side-chain of the antidepressant tianeptine is biotransformed by fatty acid β-oxidation (Fromenty, et al. (1989) *Biochem. Pharmacol.* 38:3743-3751). Further, 2-methyl fatty acids are substrates for β-oxidation (Mao, et al. (1995) *Arch. Biochem. Biophys.* 321:221-228). Accordingly, the antioxidant prodrugs of the present invention can be activated by one or more enzymes of fatty acid p-oxidation including, but not limited to, isovaleryl-CoA dehydrogenase, acyl-CoA transferase, thiolase, acyl-CoA dehydrogenase, enoyl-CoA hydratase.

A mitochondria-targeted antioxidant prodrug of the present invention finds application in methods of decreasing the degree of mitochondrial dysfunction resulting from changes in the mitochondrial redox environment and preventing or treating a disease associated with mitochondrial dysfunction. As such, antioxidant prodrugs disclosed herein can be used alone or in admixture with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier or vehicle, e.g., a liquid or solid filler, diluent, excipient, or solvent encapsulating material, is involved in carrying or transporting the antioxidant prodrug from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and other antioxidants can also be present in the compositions.

The compositions of the present invention can be administered parenterally (for example, by intravenous, intraperitoneal, subcutaneous or intramuscular injection), topically (including buccal and sublingual), orally, intranasally, intravaginally, or rectally according to standard medical practices.

The selected dosage level will depend upon a variety of factors including the activity of the particular antioxidant, the route of administration, the time of administration, the rate of excretion or metabolism of the particular compound being employed, the duration of the treatment, other drugs and/or materials used in combination with the particular antioxidant employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of an antioxidant and increase or decrease the levels as required in order to achieve the desired therapeutic effect. This is considered to be within the skill of the artisan and one can review the existing literature on a specific compound or similar compounds to determine optimal dosing.

Traditionally, mitochondrial diseases have focused on mitochondrial respiratory-chain diseases associated with mutations of mitochondrial DNA (DiMauro and Schon (2003) *N. Engl. J. Med.* 348:2656-2668). For instance, a maternal inheritance of a point mutation in the complex I gene (ND4) causes Leber's hereditary optic neuropathy (LHON) (Wallace, et al. (1988) *Science* 242:1427-1430). The diseases that result from familial mitochondrial DNA deletions and mutations are not as common as those that result from nuclear DNA defects. This may be because mitochondria contain several copies of their genome; hence, continuous fusion of mitochondria mixes the modified genes with the normal genes so that deleterious effects are reduced. Moreover, the continuous fission of mitochondria increases the likelihood that modified mitochondrial genes are removed by autophagy (Scheffler (1999) *Mitochondria*, Wiley-Liss, New York).

The realization that acute and chronic stresses to the cells lead to structural and functional impairments of mitochondria has redefined the role of mitochondria in disease etiology. Mitochondrial dysfunction resulting from changes in the mitochondrial redox environment triggers signaling cascades for necrosis and apoptosis of cells and results in organ failure and diseases. The list of diseases associated with changes in the mitochondrial redox environment includes, among others, cancer, heart failure, diabetes, obesity, stroke, neurodegenerative diseases, atherosclerosis, sepsis, and aging. As a result of changes in the mitochondrial redox environment these diseases all share the common features of disturbances of mitochondrial $Ca^{2+}$, ATP, or ROS metabolism (Brookes, et al. (2004) *Am. J. Physiol.* 287:C817-C8330). For example, cancer cells show noticeable variation in their metabolic regulation and mitochondrial morphology and physiology compared with normal cells (Decaudin, et al. (1998) *Int. J. Oncol.* 12:141-152; Modica-Napolitano and Singh (2002) *Expert Rev. Mol. Med.* 2002:1-19). Antioxidants have been used to increase efficacy of anticancer therapeutic agents by reducing their adverse effects on normal cells (Lamson and Brignall (1999) *Altern. Med. Rev.* 4:304-329). Similarly, mitochondrial dysfunction contributes to the progression of neurogenerative diseases, e.g., Parkinson's disease and stroke (Mattson (2003) *Neuromol. Med.* 3:65-94; Stavrovskaya and Kristal (2005) *Free Radic. Biol. Med.* 38:687-697). Myocardial ischemia-reperfusion injury also results in mitochondrial $Ca^{2+}$ overload that subsequently leads to uncontrollable ROS generation and opening of mitochondrial permeability transition pore (Brookes, et al. (2004) supra). Therefore, a mitochondria-targeted antioxidant prodrug of the present invention can be used for decreasing mitochondrial dysfunction by minimizing mitochondrial $Ca^{2+}$ overload, decreasing mitochondrial ROS accumulation, or improving mitochondrial energy production. In this regard, prevention and treatment of the above-mentioned diseases is achieved.

Accordingly, the present invention is also a method of using the instant mitochondria-targeted antioxidant prodrug for decreasing the degree of mitochondrial dysfunction resulting from changes in the mitochondrial redox environment. This method of the invention involves contacting a cell with an effective amount of a mitochondria-targeted antioxidant prodrug such that upon activation by an enzyme of mitochondrial fatty acid beta-oxidation, the antioxidant is released from its prodrug form and decreases mitochondrial dysfunction. Depending on the action of the antioxidant, effectiveness of a mitochondria-targeted antioxidant prodrug can be monitored using any established method. For example, protection of mitochondria from oxidative damage and apoptosis is measured by determining lipid peroxidation (thiobarbituric acid reactive species), cytochrome c release, caspase-3 activation, DNA fragmentation, inactivation of complex I and aconitase, expression of transferrin receptor, mitochondrial iron uptake, and mitochondrial membrane potential. Moreover, uptake can be monitored using a nitrobenzofurazan derivative as disclosed herein.

As will be readily appreciated by one of skill in the art, the instant prodrugs may also exhibit some antioxidative activities in the cytoplasm once they are activated and leave the mitochondria. Thus, while antioxidative actions primarily occur in the mitochondria, antioxidative activity is contemplated within the cellular domain from the plasmalemma through the cytoplasm, to golgi, to endoplasmic reticulum, to the mitochondria.

As indicated supra, the instant antioxidant prodrugs are also useful in the prevention and treatment of diseases or conditions associated with mitochondrial dysfunction resulting from changes in the mitochondrial redox environment. Prevention or treatment is achieved by administering to a subject an effective amount of a pharmaceutical composition of the present invention such that at least one sign or symptom of the disease or condition is ameliorated, delayed or inhibited. The amount administered can be dependent upon the disease to be treated, antioxidant being employed, and the pharmacokinetics and pharmacodynamics of the drug in the subject being treated.

Efficacy for the prevention and treatment of diseases or conditions associated with mitochondrial dysfunction can be monitored in a variety of well-established animal model systems for the diseases and conditions disclosed herein. For example, cardiac ischemia-reperfusion injury, which is associated with mitochondrial oxidative damage, can be investigated in a rat model (Adlam, et al. (2005) *FASEB J.* 19:1088-1095), wherein rats are given the antioxidant prodrug for a specified amount of time and observed for treatment-related effects on behavior or gross pathology. At the end of the treatment period, the hearts are removed and perfused in a Langendorff apparatus, which allows assessment of ventricular contractile function and left ventricular diastolic pressure (LVDP). After equilibration, the hearts are subjected to global zero-flow ischemia followed by normoxic reperfusion. LVDP, left ventricular pressure against time (dP/dt max), coronary blood flow, and heart rate are determined to assess efficacy.

The invention is described in greater detail by the following non-limiting examples.

Example 1

Fatty Acid β-Oxidation Activation of Phenol- and Pyridinol-Based Antioxidant Prodrugs 4-Thia- and 4-oxaalkanoic acids are biotransformed to alkanols and alkanethiols, respectively (Lau, et al. (1988) *Biochemistry* 27:5089-5095). Biotransformation of a generic 4-oxaalkanoate is presented in Scheme 1.

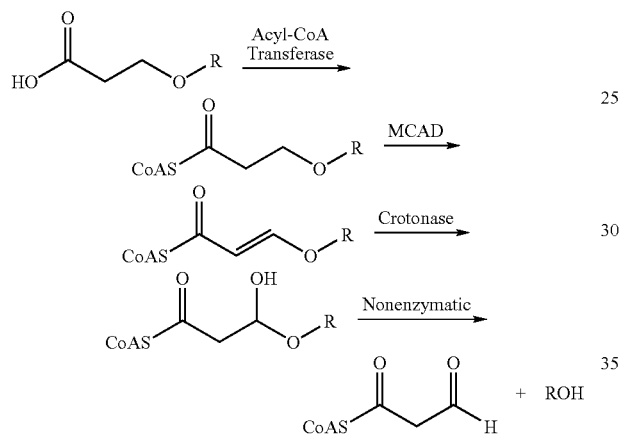

This reaction is catalyzed by the enzymes of fatty acid β-oxidation, which are localized in mitochondria. Using this catalytic activity, a variety of ROH or RSH groups can be delivered exclusively to mitochondria.

For example, phenolic antioxidants and 6-amino-3-pyridinols targeted to the mitochondria can be produced. Chain-breaking antioxidants, such as 2,6-dimethyl-4-methoxyphenol and α-tocopherol, inhibit lipid peroxidation.

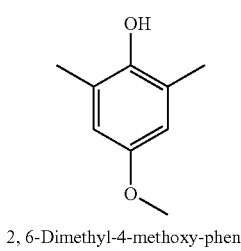 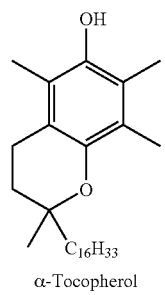

2,6-Dimethyl-4-methoxy-phenol     α-Tocopherol

This group of antioxidants inhibits peroxidation by transferring their phenolic H atoms to the propagating radicals at a rate faster than that of chain propagation. The properties of a range of phenolic antioxidants have been determined by computational analysis (Wright, et al. (1997) *J. Am. Chem. Soc.* 119:4245:4252).

Moreover, a series of 6-amino-3-pyridinols, e.g., 1 and 2, has been found to be more effective than other phenolic antioxidants (Wijtmans, et al. (2003) *Angew. Chem. Int. Ed. Engl.* 42:4370-4373).

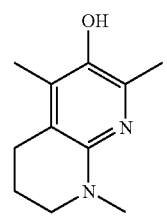

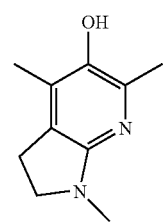

Pyridinol ethers 3 and 4 are the corresponding 4-oxabutanoic acid-based prodrugs of pyridinols 1 and 2.

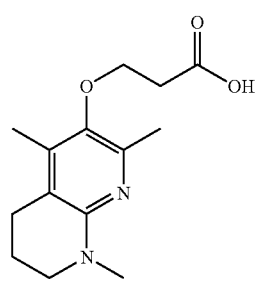

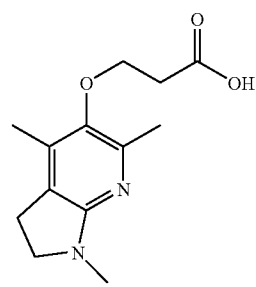

The synthesis of such antioxidants is achieved by the method disclosed in U.S. Pat. No. 6,770,672, incorporated herein by reference in its entirety, which discloses the synthesis of tocopherols, tocotrienols, and the like. Using this method, the chain lengthened analog, 3-(2,2,5,7,8-pentamethylchroman-6-yl)pentanoic acid, was synthesized. This prodrug is activated by fatty acid beta-oxidation conversion of the pentanoic acid analog to the propanoic acid followed by one more cycle of beta-oxidation, affording 2,2,5,7,8-pentamethylchroman-6-ol, the desired antioxidant.

Example 2

Fatty Acid β-Oxidation Activation of 4-Mercaptoimidzale (Ovothiol)-Based Antioxidant Prodrugs Ovothiols are natural products found in sea urchins. The fertilization of sea urchin eggs is accompanied by the release of hydrogen peroxide, which results in the formation of a protective envelope by crosslinking tyrosine residues. The sea urchin egg is protected from the deleterious effects of hydrogen peroxide by the concomitant release of redox active 4-mercaptohistidines, termed ovothiols (Shapiro (1991) Science 252:533-536; Turner, et al. (1986) J. Biol. Chem. 261: 13056-1 3063).

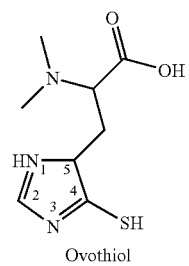

Ovothiol

The redox activity of ovothiols is attributable to their ability to scavenge free radicals and their ability to function as nonenzymatic peroxidases (Shapiro & Hopkins (1991) Adv. Enzymol. 64, 291-3 16). The chemical property of ovothiols that contributes to their antioxidant potential, and distinguishes them from glutathione, is the $pK_a$ of the thiol group. The $pK_a$ of the thiol group of 1,5-dimethyl-4-mercaptoimidazole is 2.3 (Holler & Hopkins (1988) J. Am. Chem. Soc. 110:4837-4838); hence, at pH 7.0, mercaptoimidazoles exist almost completely (99.9%) in the imidazolium thiolate form. In contrast, the $pK_a$ of the thiol group of glutathione is 8.6; at pH 7.0, glutathione exists largely (>90%) as the thiol. Accordingly, ovothiols react with iodoacetamide nine-times faster than glutathione. Ovothiols are effective scavengers of free radicals (Holler & Hopkins (1990) Biochemistry 29:1953-1961). 1,5-Dimethyl-4-mercaptoimidazole is much more effective than glutathione in reducing Fremy's salt and Banfield's radical. Hence, ovothiols are kinetically superior to glutathione in reducing free radicals, and this kinetic superiority is attributable to the resonance stabilization by the imidazole group.

Ovothiols may also serve as two-electron reductants. Ovothiols react more rapidly than glutathione with hydrogen peroxide (Turner, et al. (1988) Science 242:939-941); the second-order rate constants for the reaction of ovothiols and glutathione with hydrogen peroxide are 2.0 $s^{-1}$ $M^{-1}$ and 0.43 $s^{-1}$ $M^{-1}$, respectively.

The preparation and analysis of a panel of ovothiol-derived 4-mercaptoimidazoles has been described (Zoete, et al. (1997) J. Chem. Soc., Perkin Trans. I, 2983-2988). These studies showed that compounds bearing an electron-withdrawing group (3-$ClC_6H_4$, 2-$ClC_6H_4$, 2-$CF_3C_6H_4$, 3-$CF_3C_6H_4$, $CF_3$) at C-2 had the highest radical scavenging ability. Subsequent studies have shown that these compounds are powerful scavengers of HOCl and are more potent than N-acetylcysteine (Zoete, et al. (2000) Free Radic. Res. 32:515-524). The radical-scavenging mechanism of 4-mercaptoimidazoles was studied by QSAR, cyclic voltammetry, ESR, and NMR spectroscopy, and a significant correlation was found between the DPPH scavenging abilities of the 4-mercaptoimidazoles and thermodynamic parameters (Zoete, et al. (2000) Free Radic. Res. 32:525-533).

Accordingly, mitochondria-targeted ovothiol-based prodrugs are disclosed herein for use in specifically scavenging mitochondrial ROS. A variety of 4-mercaptoimidazole antioxidants are well-known in the art (Spaltenstein, et al. (1987) J. Org. Chem. 52, 2977-2979; U.S. Pat. No. 4,898,878) and can be employed as reagents for the synthesis of mitochondria-targeted ovothiol-based prodrugs. For example, 1,5-dimethyl-4-mercaptoimidazole 6 with either ethyl acrylate 7 (Scheme 3) or ethyl 3-bromopropanoate 8 (Scheme 4) will, after hydrolysis of the ester (ethyl 3-(1,5-dimethyl-1H-imidazol-4-ythio)propanoate 9), give the desired sulfide, 3-(1,5-dimethyl-1H-imidazol-4-ythio)propanoic acid 10.

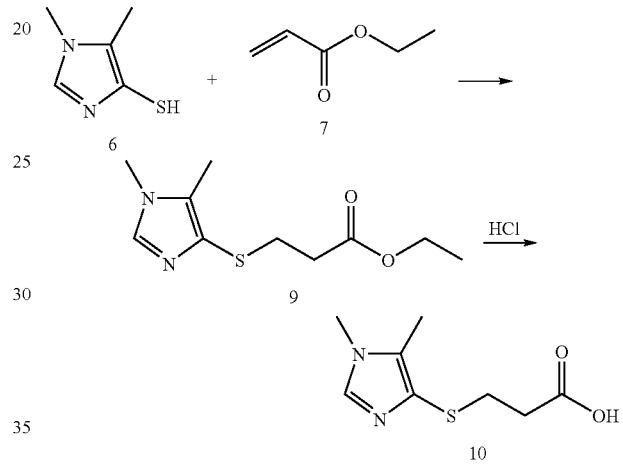

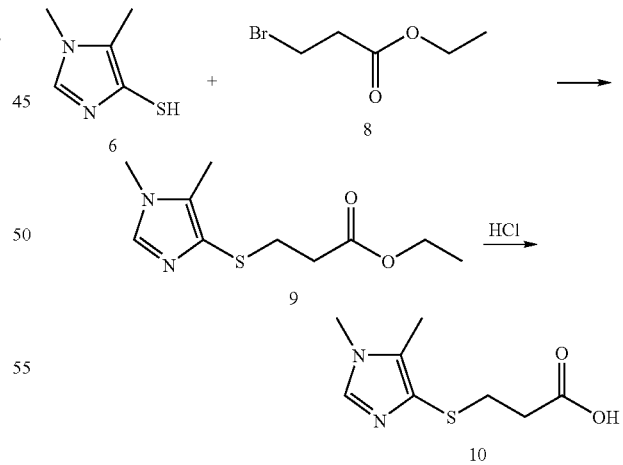

Example 3

Fatty Acid β-Oxidation Activation of 3-Aminoxypropanoic Acid-Based Antioxidants Although hydroxylamine ($HONH_2$) has long been known to possess anticancer activity and to delay senescence in mice (Harman (1961) *J. Gerontol. A Biol. Sci. Med. Sci.* 16:247-254), the observation of the retardation of senescence and the radioprotective effects of N-alkylhydroxylamines has only recently been reported. The spin-trapping compound α-phenyl-N-tert-butylnitrone (PBN) exerts well-described anti-aging effects in vivo, delays senescence of normal human lung fibroblasts (IMR90), and has radioprotective effects in vivo (Kotake (1999) *Antioxid. Redox Signal.* 1:481-499; Lee & Park (2003) *Cancer Res.* 63:6885-6893). The observations that PBN decomposes to give N-tert-butylhydroxylamine and that old solutions of PBN are more effective than freshly prepared solutions of PBN in delaying senescence in IMR90 cells lead to the investigation of the antioxidant properties of N-tert-butylhydroxylamines and related N-substituted hydroxylamines (Chamulitrat, et al. (1995) *Free Radic. Res.* 23:1-14; Atamna, et al. (2000) *J. Biol. Chem.* 275:6741-6748).

N-tert-butylhydroxylamine, N-methylhydroxylamine, and N-benzylhydroxylamine, but not the O-methyl, O-tert-butyl, and O-benzyl analogs, delay senescence in IMR90 cells at concentrations as low as 10 μM (Atamna, et al. (2000) supra); in addition, N-substituted hydroxylamines delay senescence-dependent changes in mitochondria, prevent the age-associated decline in mitochondrial aconitase activity, block hydrogen peroxide-induced senescence, decrease the formation of ROS and oxidant-induced DNA damage, increase the glutathione/glutathione disulfide ratio, and inhibit the reduction of cytochrome c by superoxide. These findings show that oxidative phenomena contribute to cellular senescence and that N-substituted hydroxylamines effectively retard these changes. Subsequent studies confirmed these observations and further showed that N-tert-butylhydroxylamine 11 is oxidized to N-tert-butylhydronitroxide 12 and thence to 2-methyl-2-nitrosopropane 13, which are reduced to N-tert-butylhydroxylamine by mitochondrial NADH (Atamna, et al. (2001) *FASEB J.* 15:2196-2204) (Scheme 5).

SCHEME 5

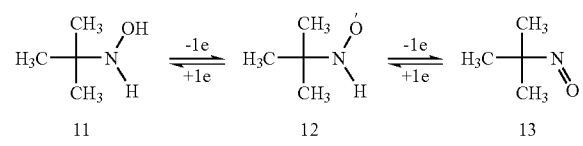

The radioprotective effects of N-tert-butylhydroxylamine have been studied in U937 cells and in mice (Lee, et al. (2004) *Carcinogenesis* 25:1435-1442). Ionizing radiation-induced cytotoxicity, cellular oxidative damage, and mitochondrial damage were all decreased by N-tert-butylhydroxylamine. Feeding N-tert-butylhydroxylamine (5 mg/kg daily for two weeks) to mice decreased the radiation sensitivity of animals subjected to 8 Gy of whole-body irradiation, and no compound-associated toxicity was observed. Although N-substituted hydroxyamines appear to induce little or no toxicity at the doses studied, hydroxylamine and O-substituted hydroxylamines are hematotoxic (Evelo, et al. (1998) *Blood Cells Mol. Dis.* 24:280-295)).

A series of 3-aminoxypropanoic acids has been synthesized as bioisosteres of antiinflammatory arylacetic acids, e.g., dichlofenac (Macchia, et al. (1990) *J. Med. Chem.* 33:1423-1430; Macchia, et al. (1995) *Farmaco* 50:83-90; EP 0 175 304). Several of these compounds show significant antiinflammatory activity in the carrageenan-induced paw edema test and some show platelet anti-aggregating activity. These compounds may, as the original experimental design proposed, serve as bioisosteres of antiinflammatory arylacetic acids; however, it is believed that these compounds may also undergo fatty acid β-oxidation-dependent metabolism to N-substituted hydroxylamines.

Accordingly, N-alkyl 3-aminoxypropanoic acids 14 are disclosed herein as antioxidant prodrugs, which upon fatty acid p-oxidation, release N-alkylhydroxylamines 15 (Scheme 6). Likewise, N-benzyl-3-aminoxypropanoic acid prodrugs are disclosed herein because these compounds also exhibit antioxidant potential and the aromatic ring imparts useful UV absorption.

SCHEME 6

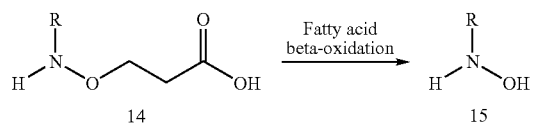

N-tert-butyl- and N-benzyl-3-aminoxypropanoic acid can be synthesized as shown in Scheme 7. N-Substituted 3-aminoxypropanoic acids are accessible by the Michael addition of the N-substituted hydroxylamines 15 to acrylamide 16 to give N-substituted 3-aminoxypropanenitriles 17 (Sayigh, et al. (1964) *J. Org. Chem.* 29:2042-2043); hydrolysis of the intermediate nitrile gives the N-substituted 3-aminoxypropanoic acids 18.

SCHEME 7

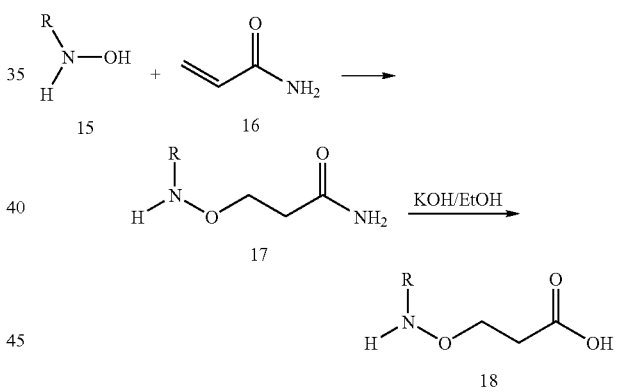

The required N-tert-butylhydroxylamine hydrochloride and benzylhydroxylamine hydrochloride are commercially available. The addition of N-alkylhydroxylamines to α,β-unsaturated esters can be considered as an alternative route to the desired 3-aminoxypropanoic acids, but reaction of hydroxylamines with α,β-unsaturated esters gives isoxazolones as products (Fountain, et al. (1975) *Tetrahedron Lett.* 3027-3030).

Example 4

Thiol-Based Antioxidant Prodrugs

4-Thiaalkanoates undergo mitochondrial β-oxidation to form butanethiol (from 4-thiaoctanoic acid; Lau, et al. (1988) *Biochemistry* 27:5089-5095). Haloalkene-derived 4-thiaalkanoates are potent mitochondrial poisons and also undergo α-oxidation-dependent bioactivation (Fitzsimmons & Anders (1993) *Chem. Res. Toxicol.* 6:662-668; Fitzsimmons, et al. (1995 supra). Hence, it is established that the mitochondrial β-oxidation can be used to deliver thiols to the mitochondria. 1,4-Dithiothreitol protects cells from S-(1,2-dichlorovinyl)-L-cysteine-induced expression of hsp70 (Chen, et al. (1992) *J. Biol. Chem.* 267:24322-24327), indicating a role for thiols in cytoprotection.

Accordingly, 2-(1,3-dithiolan-2-yl)acetic acid 19 (Scheme 8) and 2-(1,3-dithian-2-yl)acetic acid 20 (Scheme 9) are useful prodrug forms of cytoprotective dithiols. Both compounds can be considered to be analogs of isovaleric acid (3-methylbutanoic acid). Isovaleryl-CoA dehydrogenase catalyzes the conversion of isovaleryl-CoA to 3-methylcrotonyl-CoA (Finocchiaro, et al. (1987) *J. Biol. Chem.* 262:7982-2989), which is converted by enoyl-CoA hydratase to 3-hydroxyvaleryl-CoA. As such, 2-(1,3-dithiolan-2-yl)acetic acid 19 would yield ethane-1,2-dithiol 21 as a terminal product. With 2-(1,3-dithian-2-yl)acetic acid 20 as the substrate, the terminal product would be propane-1,3-dithiol 22.

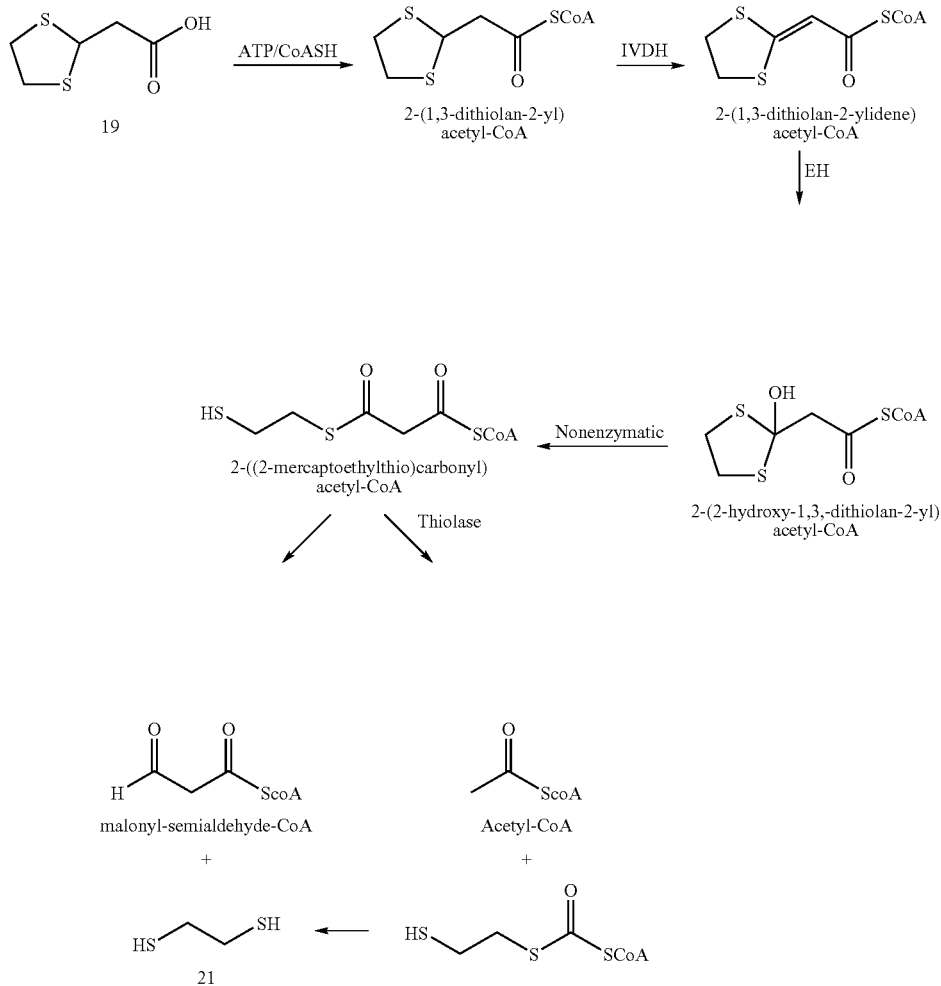

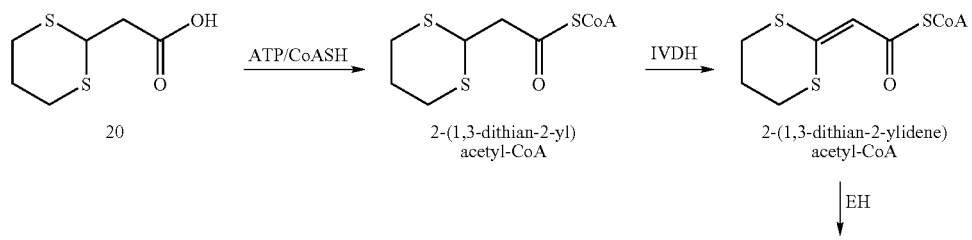

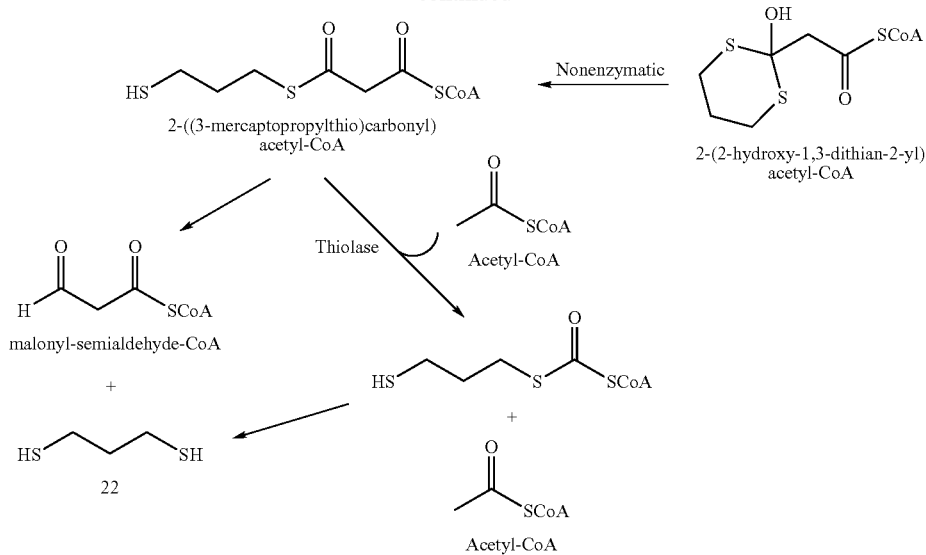

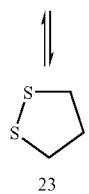

Unlike ethane-1,2-dithiol 21, propane-1,3-dithiol 22 can be oxidized (by analogy to 1,4-dithiothreitol) to 1,2-dithiolane 23. 2-((2-Mercaptoethylthio)carbonyl)acetyl-CoA and 2-((3-mercaptopropylthio)carbonyl)acetyl-CoA can be readily hydrolyzed or can serve as a substrate for 3-oxoacyl-CoA thiolase.

Synthesis of both (1,3-dithian-2-yl)acetic acid 20 and (1,3-dithiolan-2-yl)acetic acid 19 is shown in Scheme 10. The syntheses start with commercially available (Aldrich) methyl 3,3-dimethoxypropionate 24. Cleavage of the dimethylacetal and reaction of the resulting aldehyde with ethane-1,2-dithiol or propane-1,3-dithiol would give methyl 2-(1,3-dithioian-2-yl)acetate and methyl 2-(1,3-dithian-2-yl)acetate, respectively. Hydrolysis of the esters would give 2-(1,3-dithiolan-2-yl)acetic acid 19 and 2-(1,3-dithian-2-yl)acetic acid 20. An alternative route to (1,3-dithiolan-2-yl)acetic acid has been reported (Jones & Kropp (1974) *Synthetic Commun.* 4:331-334).

SCHEME 10

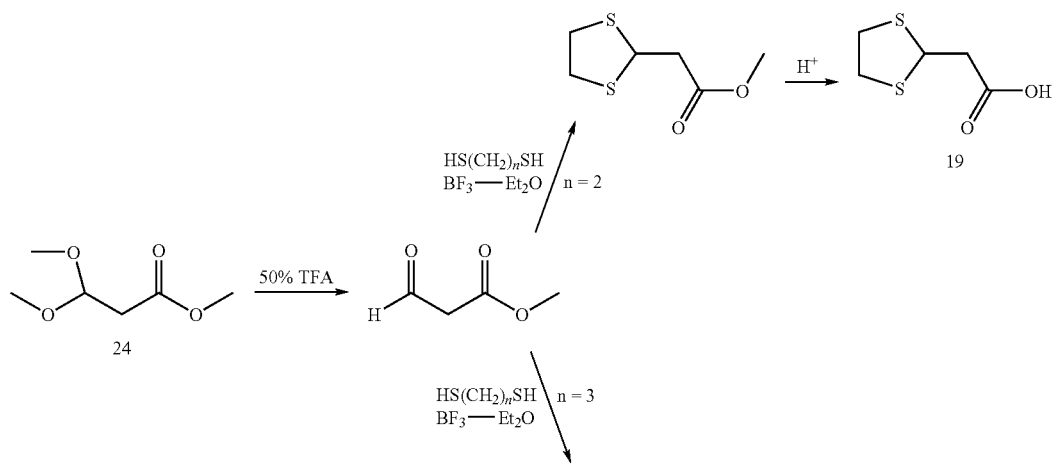

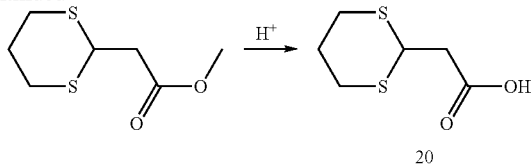

Example 5

Mitochondrial Biotransformation of ω-(Phenoxy) Alkanoic Acids, 3-(Phenoxy)Acrylic Acids, and ω-(1-Methyl-1h-imidazol-2-ylthio)Alkanoic Acids Mitochondrial β-oxidation of a series of ω-(phenoxy)alkanoic acids and 3-(phenoxy)acrylic acids to the corresponding phenols and of ω-(1-methyl-1H-imidazol-2-ylthio)alkanoic acids to methimazole was analyzed (FIG. 1). The compounds analyzed are shown in Table 1.

TABLE 1

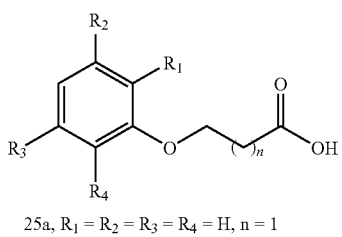

25a, $R_1 = R_2 = R_3 = R_4 = H$, n = 1
25b, $R_1 = CH_3$, $R_2 = R_3 = R_4 = H$, n = 1
25c, $R_1 = R_4 = CH_3$, $R_2 = R_3 = H$, n = 1
25d, $R_1 = R_4 = H$, $R_2 = R_3 = CH_3$, n = 1
26a, $R_1 = R_2 = R_3 = R_4 = H$, n = 3
26b, $R_1 = CH_3$, $R_2 = R_3 = R_4 = H$, n = 3
26c, $R_1 = R_4 = CH_3$, $R_2 = R_3 = H$, n = 3

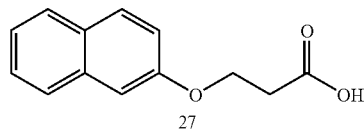 [SMILES: O=C(O)CCOc1ccc2ccccc2c1]

27

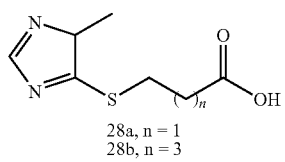

28a, n = 1
28b, n = 3

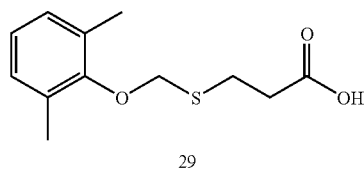 [SMILES: Cc1cccc(C)c1OCSCCC(=O)O]

29

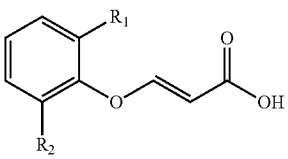

30a, $R_1 = R_2 = CH_3$
30b, $R_1 = R_2 = CH(CH_3)_2$

Methods.

HEPES, EGTA (Sigma E4378), sucrose, ATP disodium salt (Sigma A7699), CoA (Sigma C3144), KCl, $MgCl_2 \cdot 6H_2O$, and L-carnitine were purchased from Sigma-Aldrich (St. Louis, Mo.). $KH_2PO_4$ was obtained from JT Baker; and D,L-dithiothreitol was purchased from TCI America (Boston, Mass.). Chemicals for organic synthesis were obtained from Aldrich (Milwaukee, Wis.). 3-(Phenoxy)propanoic acid 25a was purchased from Aldrich. 3-(2-Methylphenoxy)propanoic acid 25b was obtained from UkrOrgSynthesis (Kiev, Ukraine). 3-(2,6-Dimethylphenoxy)propanoic acid 25c was prepared as described by Lichtenberger et al. (1962) Bull. Soc. Chim. Fr. 997). 3-(3,5-Dimethylphenoxy)propanoic acid 25d was purchased from UkrOrgSynthesis. 5-(Phenoxy)pentanoic acid 26a was obtained from TCI America (Boston, Mass.).

The synthesis of 5-(2-methylphenoxy)pentanoic acid 26b was prepared from 2-methylphenol and methyl 5-bromopentanoate by established methods (Sanders, et al. (2004) Research Development Foundation, Carson City, Nev.) 11). $^1$H NMR: (400 MHz, CDCl$_3$) 1.83-1.90 (m, 4H), 2.22 (s, 3H), 2.44-2.48 (t, 2H, J=7.0 Hz), 3.96-3.99 (t, 2H, J=5.8 Hz), 6.78-7.15 (m, 4H), 11 (br s, 1H). MS (ESI): 231 [M+Na]$^+$.

5-(2,6-Dimethylphenoxy)pentanoic acid 26c was prepared in the same manner as 26b, except that 2,6-dimethylphenol was used as the starting material. $^1$H NMR: (400 MHz, CDCl$_3$): 7.0-7.1 (m, 3H), 3.83 (t, 2H, J=6 Hz), 2.37 (t, 2H, J=6 Hz), 2.73 (s, 6H), 1.92 (m, 4H). MS (ESI): 223 [M+H]$^+$; 245 [M+Na]$^+$.

5-(3,5-Dimethylphenoxy)pentanoic acid 26d was prepared in the same manner as 26b, except that 3,5-dimethylphenol was used as the starting material. $^1$H NMR (CDCl$_3$, 400 MHz): 6.58 (s, 1H), 6.51 (s, 2H), 3.94 (t, 2H, J=5.6 Hz), 2.44 (t, 2H, J=7.2 Hz), 2.27 (s, 6H), 1.83 (m, 4H). MS (ESI): 245 [M+Na]$^+$.

3-(2-Naphthoxy)propanoic acid 27 was prepared as described by Bel & Duewel (1963) Austral. J. Chem. 16:101.

3-(1-methyl-1H-imidazol-2-ylthio)propanoic acid 28a was prepared as described for 5-(1-methyl-1H-imidazol-2-ylthio)pentanoic acid (Tweit, et al. (1973) J. Med. Chem. 16:1161), except that 3-bromopropanoic acid was used as the starting material. $^1$H NMR (400 MHz, CDCl$_3$): 2.62-2.65 (t, 2H, J=6.4 Hz), 3.13-3.16 (t, 2H, J=6.4 Hz), 3.73 (s, 3H), 7.34-7.35 (d, 1H, J=2.1 Hz), 7.38-7.39 (d, 1H, J=2.1 Hz), 11 (br s, 1H). MS (ESI): 187 [M+H]$^+$.

5-(1-Methyl-1H-imidazol-2-ylthio)pentanoic acid 28b was synthesized as described by Tweit, et al. (1973) supra.

3-([2,6-Dimethylphenoxy]methylthio)propanoic acid 29 was prepared by reaction of 2-(chloromethoxy)-1,3-dimethylbenzene with methyl 3-mercaptopropanoate followed by hydrolysis of the ester. 2-(Chloromethoxy)-1,3-dimethylbenzene: A three-necked, 500-mL flask equipped with thermometer, reflux condenser, argon inlet, and a magnetic stirring bar was charged with 6.12 g (0.05 mol) of 2,6-dimethylphenol, 100 mL dry tetrahydrofuran, and 4.0 g (0.1 mol) sodium hydroxide powder. The mixture was heated at 66° C. for 1 hour. The mixture was cooled to room temperature, and 98 mL (1.5 mol) of bromochloromethane was added. The suspension that formed was cooled to room temperature, filtered through CELITE, and the solvent was removed under reduced pressure. The oily residue was purified by vacuum distillation (1-1.5 torr, b.p., 66° C.) to afford an overall yield of 6.50 g (76%) of 2-(chloromethoxy)-1,3-dimethylbenzene. $^1$H NMR (400 MHz, CDCl$_3$): 2.33 (s, 6H), 5.80 (s, 2H), 6.99-7.06 (m, 3H).

Methyl 3-[(2,6-dimethylphenoxy)methylthio]propanoate: A mixture of 2.40 g (20 mmol) of methyl 3-mercaptopropionate, 2.58 g (20 mmol) of diisopropylethylamine, and 1.70 g (100 mmol) of 2-(chloromethoxy)-1,3 dimethylbenzene in 40 mL of dry tetrahydrofuran under argon was heated at reflux for 52 hours. The reaction mixture was cooled, diluted with 60 mL methylene chloride, and extracted with 5% HCl. The organic phase was extracted twice with 30 mL of distilled water, then with 40 mL of saturated sodium chloride solution, and dried with anhydrous magnesium sulfate. The solvent was removed under reduced pressure, and 3.20 g of yellowish oil was obtained. The product was purified by normal-phase chromatography (COMBIFLASH; Teledyne Isco, Inc., Lincoln, Nebr.) with a hexane/ethyl acetate gradient (100:0, 5 minutes, 95:5, 15 minutes) to afford 2.20 g (87%) of methyl 3-[(2,6-dimethylphenoxy)methylthio]propanoate. $^1$H NMR (400 MHz, CDCl$_3$): 2.32 (s, 6H), 2.78-2.82 (t, 2H, J=7.2 Hz), 3.03-3.07 (t, 2H, J=7.2 Hz), 3.70 (s, 3H), 4.07 (s, 2H), 6.92-7.02 (m, 3H).

3-[(2,6-Dimethylphenoxy)methylthio]propanoic acid 29: A 50-mL flask equipped with reflux condenser and a magnetic stirring bar was charged with 0.254 g (1 mmol) of methyl 3-[(2,6-dimethylphenoxy)methylthio]propanoate and 0.362 g (2 mmol) of trimethyltin hydroxide dissolved in 25 mL of 1,2-dichloroethane and was refluxed overnight under an argon atmosphere. The solvent was removed under reduced pressure, the organic residue was dissolved in 40 mL of ethyl acetate, extracted 3 times with 10 mL 5% HCl, then with 10 mL brine, and dried with anhydrous magnesium sulfate. The solvent was removed under reduced pressure, and the reddish residue was purified by normal-phase (COMBIFLASH) chromatography with a hexane/ethyl acetate (95:5, 7 minutes; 95:40, 15 minutes) to afford 0.2 g (83%) of 3-[(2,6-dimethylphenoxy)methylthio]propanoic acid 29. $^1$H NMR (400 MHz, CDCl$_3$): 2.33 (s, 6H), 2.78-2.82 (t, 2H, J=7.2 Hz), 3.03-3.07 (t, 2H, J=7.2H), 4.99 (s, 2H), 6.94-7.04 (m, 3H), 10.98 (b, OH). MS (ESI): 241 [M+H]$^+$; 263 [M+Na]$^+$.

(E)-3-(2,6-dimethylphenoxy)acrylic acid 30a was prepared by the general method of Fan, et al. ((2006 *Synthesis* 2286): ethyl (E/Z)-3-(2,6-dimethylphenoxy)acrylate: 2,6-Dimethylphenol (1.5 g, 12.3 mmol) and 1,4-diazabicyclo[2.2.2]octane (100 mg, 0.9 mmol) and 2 mL of methylene chloride were combined with magnetic stirring. Ethyl propiolate (1.2 mL, 12.6 mmol) in 3 mL of methylene chloride was added drop wise over 5-10 minutes. Thin-layer chromatography of the reaction mixture (silica gel, hexane) showed the formation of two products. The reaction mixture was diluted with ~70 mL of ethyl acetate and extracted with 10% potassium hydroxide, and then with saturated sodium chloride solution. The mixture was then extracted with 10% hydrochloric acid solution and then again with saturated sodium chloride solution. The ethyl acetate extract was dried with anhydrous magnesium sulfate, filtered, and evaporated to dryness to afford 2.9 g (100%) of product. A sample of this material (1.0 g) was purified by normal-phase chromatography (COMBIFLASH) to afford 650 mg of ethyl (E)-3-(2,6-dimethylphenoxy)acrylate [$^1$H NMR (400 MHz, CDCl$_3$): 1.24 (t, 3H, J=7.2 Hz), 2.17 (s, 6H), 4.13 (q, 2H, J=7.2 Hz), 5.00 (d, 1H, J=12.4 Hz), 7.04 (m, 3H), 7.74 (d, 1H, J=12.4 Hz], and 300 mg of the ethyl (Z)-3-(2,6-dimethylphenoxy)acrylate [$^1$H NMR (400 MHz, CDCl$_3$): 1.31 (t, 3H, J=7.2 Hz), 2.24 (s, 6H), 4.23 (q, 2H, J=7.2 Hz), 5.02 (d, 1H, J=6.8 Hz), 6.46 (d, 1H, J=6.8 Hz), 7.02 (m, 3H)]. (E)-3-(2,6-Dimethylphenoxy)acrylic acid 30a. Three hundred milligrams of ethyl (E)-3-(2,6-dimethylphenoxy)acrylate was combined with 0.5 g of KOH in 10 mL of a 20:80 mixture of water/ethanol and heated at reflux for 2.5 hours. The progress of the reaction was monitored by thin-layer chromatography (silica gel, hexane/ethyl acetate, 95:5). When the reaction had gone to completion, the reaction mixture was removed from heat and the ethanol was removed under reduced pressure. The reaction mixture was acidified with 5% hydrochloric acid solution and extracted with three 30-mL portions of ethyl acetate. The ethyl acetate solution was washed with saturated sodium chloride solution, dried with anhydrous sodium sulfate, and the solvent was removed under reduced pressure. The solid that formed was titrated with hexane and collected by vacuum filtration to afford 100 mg of (E)-3-(2,6-dimethylphenoxy)acrylic acid 30a. NMR (400 MHz, CDCl$_3$): 2.17 (s, 6H), 5.00 (d, 1H, J=12.4 Hz), 7.05 (s, 3H), 7.80 (d, 1H, J=12.4 Hz), 11.0 (br s, 1H). MS (ESI): 215 [M+Na]$^+$.

(E)-3-(2,6-diisopropylphenoxy)acrylic acid 30b was also prepared by the general method of Fan, et al. ((2006) supra): ethyl (E/Z)-3-(2,6-diisopropylphenoxy)acrylate. 2,6-Diisopropylphenol (2.0 g, 11.3 mmol), 1,4-diazabicyclo[2.2.2]octane (122 mg, 1 mmol), and 10 mL of methylene chloride were combined with magnetic stirring. Ethyl propiolate (1.20 mL, 116 mmol) in 4 mL of methylene chloride was added drop wise over 10 minutes. The reaction mixture was refluxed overnight and was then was diluted with 85 mL of ethyl acetate and extracted with 10% potassium hydroxide solution, with 10% hydrochloric acid solution, and then with saturated sodium chloride solution. The ethyl acetate layer was dried with anhydrous magnesium sulfate and filtered. The solvent was removed under reduced pressure to afford 2.72 g (87% yield) of a mixture of E- and Z-isomers of the product. The isomeric mixture (500 mg) was separated and purified by normal-phase chromatography (COMBIFLASH) with a hexane/ethyl acetate gradient (95:5, 6 minutes; 80:20, 10 minutes) to afford 325 mg (65%) of ethyl (E)-3-(2,6-diisopropylphenoxy)acrylate. $^1$H NMR (400 MHz, CDCl$_3$): 1.17-1.19 (d, 12H), 1.22-1.26 (t, 3H, J=7.2), 3.00-3.07 (m, 2H), 4.11-4.17 (q, 2H), 5.06-5.09 (d, 1H, J=12.4 Hz), 7.14-7.22 (m, 3H), 7.74-7.77 (d, 1H, J=12.4 Hz).

(E)-3-(2,6-Diisopropylphenoxy)acrylic acid 30b. Ethyl (E)-3-(2,6-diisopropylphenoxy)acrylate (250 mg, 0.91 mmol) was combined with 0.5 g of solid KOH in 10 mL of a mixture of water/ethanol (20:80), and the mixture was refluxed overnight. The solvent was removed under reduced pressure. The residue was acidified with 5% HCl solution and then extracted with three 25 mL portions of ethyl acetate. The ethyl acetate solution was extracted with saturated sodium chloride solution and dried with anhydrous sodium sulfate. The solvent was removed under reduced pressure to yield 150 mg (60%) of (E)-3-(2,6-diisopropylphenoxy)acrylic acid 30b. $^1$H NMR (400 MHz, CDCl$_3$) 1.17-1.19 (d, 12H), 2.98-3.05 (m, 2H), 5.05-5.08 (d, 1H, J=12.4 Hz), 7.14-7.22 (m, 3H), 7.81-7.85 (d, 1H, J=12.4 Hz). MS (ESI): 271 [M+Na].

Mitochondrial Biotransformation of Alkanoic-Acid-Based Prodrugs. Rat liver mitochondria were isolated from livers freshly collected from adult male Sprague-Dawley rats (190-225 g) and were used as soon as possible after isolation (Nadtochiy, et al. (2007) *J. Mol. Cell. Cardiol.* 42:812; Hoffman et al. (2007) *Am. J. Physiol.* 292:H101). Livers were removed immediately after CO$_2$ euthanasia of the animal, minced, and homogenized with a glass Dounce homogenizer with loose-fitting pestle in liver mitochondria isolation medium that contained 0.25 M sucrose, 2.0 mM HEPES, 1.0 mM EGTA (pH 7.4) at 4° C. The homogenate was centrifuged once at 1000×g for 3 minutes at 4° C. to remove cellular debris. After removal of visible surface fat, the resulting supernatant was centrifuged at 10,000×g for 10 minutes at 4° C. The supernatant was discarded after removing visible surface fat, and the pellet was suspended in ice-cold liver mitochondria isolation medium and centrifuged again at 10,000×g for 10 minutes at 4° C. The mitochondrial pellet thus obtained was suspended in $Ca^{2+}$-depletion buffer (1 mM EGTA, 10 mM NaCl, 5 mM succinate, 195 mM mannitol, 25 mM sucrose, 40 mM HEPES, pH 7.2) at room temperature) and incubated with gentle stirring first at room temperature for 10 minutes and then in an ice bath for 5 minutes. $Ca^{2+}$-Depletion buffer serves to chelate calcium, activate mitochondrial respiration, and activate the $Na^+/Ca^{2+}$ exchanger. The mitochondrial suspension was then centrifuged at 10,000×g for 10 minutes at 4° C., and the pellet was suspended in liver swelling buffer that contained 195 mM mannitol, 25 mM sucrose, 40 mM HEPES (pH 7.2) at 4° C.; liver swelling buffer allows for ionic/osmotic equilibrium through the remainder of the preparation. The suspension was centrifuged at 10,000×g for 10 minutes at 4° C., followed by the removal of light mitochondria and a final centrifugation at 10,000×g for 10 minutes at 4° C. The mitochondrial pellet was suspended in liver swelling buffer at 4° C. Protein concentrations were determined with the Lowry reagent.[56]

The quality of mitochondrial preparations was determined by estimating the respiration control ratio (RCR, i.e., the ratio of state 3 vs. state 4 respiration rates) with a Clark-type oxygen electrode (Oxygraph, Hansatech Instruments, Norfolk, England). The incubation mixtures contained 120 mM KCl, 25 mM sucrose, 5 mM $MgCl_2$, 5 mM $KH_2PO_4$, 1 mM EGTA, 10 mM HEPES, 10 mM succinate, 2.5 mg/mL fat-free bovine serum albumin, 0.5-0.8 mg/mL mitochondrial protein, 5 μM rotenone, and 100 μM ADP (pH 7.4) and were incubated at 37° C. RCR ranged from 4.5 to 6.5.

Reaction mixtures were prepared in disposable glass culture tubes and contained 20 mM HEPES, 1 mM EGTA, 100 mM KCl, 5 mM $KH_2PO_4$, 10 mM $MgCl_2$, 25 mM sucrose, 2 mM L-carnitine (if added), 5 mM ATP, 10 mg/mL bovine serum albumin, 1.4 mM dithiothreitol, 0.13 mM CoA, and 1 mM substrate (pH 7.4). Reaction mixtures were incubated at 37° C. with gentle stirring. Mitochondrial protein (approximately 5 mg/mL) was added, and the samples were incubated for 5 minutes with gentle mixing, which was maintained during the incubation period, to keep the homogenate suspended. After 5 minutes of incubation, the substrates were added. The substrates were dissolved in methanol and added to the reaction mixtures to a final concentration of 1 mM, unless otherwise stated; the final methanol concentration was ≤0.5%. ω-(1-Methyl-1H-imidazol-2-ylthio)alkanoic acids 28a and 28b were dissolved in distilled water and added to the reaction mixtures to a final concentration of 1 mM. Samples were incubated at 37° C. for 30 minutes with constant gentle mixing, and samples were collected for analysis at t=0, 10, 20, and 30 minutes.

Analyses.

Phenolic metabolite formation, i.e., phenol, 2-methylphenol, 2,6-dimethylphenol, 3,5-dimethylphenol, and 2,6-diisopropylphenol, from ω-(phenoxy)alkanoic acids, was quantified by HPLC analysis. Two hundred microliters of the reaction mixture was added to 200 μL of acetonitrile; the mixtures were mixed and then sonicated in a BRANSON ultrasonic water bath (Danbury, Conn.) for 5-10 minutes. The denatured sample mixtures were centrifuged at 15,000-16,000×g for 5 minutes. Supernatants were analyzed with an AGILENT 1100 series HPLC (Santa Clara, Calif.) with UV detection at 265 and 272 nm. A 5 μL sample of the supernatant was injected onto a PHENOMENEX SYNERGI Hydro-RP analytical column (150 mm×2.0 mm, 4 μm particle size, 80 Å pore, 30° C.). The column was eluted at a flow rate of 0.4 mL/minute with 0.1% (v/v) formic acid (solvent A) and acetonitrile (solvent B) with this gradient: 15% B for 5 minutes, increased to 95% B over 20 minutes, held at 95% B for 10 minutes, and returned to 15% B in 2 minutes. The column was equilibrated with 15% B for 10 minutes before the next sample was analyzed.

In some experiments, phenolic metabolites of ω-(phenoxy) alkanoic acids were analyzed by LC-MS on an AGILENT 1100 LC/MSD ion trap with electrospray ionization (ESI) interface in either positive- or negative-ion, smart-tune mode (nebulizer pressure, 30 psi; dry gas flow (nitrogen), 8 Lpm; dry temperature, 350° C.) with the same HPLC parameters as described above.

Methimazole formation from ω-(1-methyl-1H-imidazol-2-ylthio)alkanoic acids 28a and 28b was quantified by adding 200 μL of the reaction mixture to 10 μL of 70% perchloric acid followed by mixing. The mixtures were centrifuged at 15,000-16,000×g for 5 minutes. Samples of the supernatants were analyzed by HPLC (AGILENT 1100 series) with UV detection at 250 nm. A 5 μL sample of the supernatant was injected onto a PHENOMENEX SYNERGI Hydro-RP analytical column (150 mm×2.0 mm, 4 μm particle size, 80 Å pore) held at 30° C. The column was eluted with 5 mM sodium 1-heptanesulfonate monohydrate (Fluka) (solvent A) and acetonitrile (solvent B) at a flow rate of 0.4 mL/minute with this gradient: 100% A for 5 minutes, increased to 30% B over 15 minutes, held at 30% B for 5 minutes, increased to 90% B over 5 minutes, held at 90% B for 5 minutes, and returned to 100% A over 3 minutes. The column was equilibrated with 100% A for 10 minutes before the next sample was analyzed.

The mitochondrial biotransformation of octanoic acid was measured using standard methods (Bjorge & Baillie (1991) *Drug Metab. Dispos.* 19:823).

Biological Evaluation.

The cytoprotective effects of ω-(1-methyl-1H-imidazol-2-ylthio)alkanoic acids 28a and 28b, 3-(2,6-dimethylphenoxy) propanoic acid 25c, and 3-(2,6-dimethylphenoxy)acrylic acid 30a were investigated in cardiomyocytes. Primary ventricular cardiomyocytes were isolated from adult rats and viability was assessed (Lowry, et al. (1951) *J. Biol. Chem.* 193:265). All cells were used within 1 hour of isolation and were 80-85% viable and rod-shaped prior to the experiments. Cell viability was quantified with the Trypan Blue exclusion test. The cells were subjected to a hypoxia-reoxygenation protocol designed to simulate cardiac ischemia-reperfusion injury. The cells were divided into four treatment groups: (i) control: cells were incubated under an atmosphere of 95% $O_2$/5% $CO_2$ in Krebs-Henseleit buffer, pH 7.4; (ii) hypoxia-reoxygenation (HR): cells were incubated for 1 hour under an atmosphere of 95% $N_2$/5% $CO_2$ in glucose-free 50 mM HEPES buffer, pH 6.5, followed by incubation for 30 minutes in the reoxygenation medium (95% $O_2$/5% $CO_2$, glucose-containing Krebs-Henseleit buffer, pH 7.4); (iii) HR conditions except that ω-(1-methyl-1H-imidazol-2-ylthio)alkanoic acids 28a and 28b, 3-(2,6-dimethylphenoxy) propanoic acid 25c, and 3-(2,6-dimethylphenoxy)acrylic acid 30a were added 20 minutes before incubation under HR conditions; (iv) HR conditions (see iii) except that etomoxir was added 10 minutes before ω-(1-methyl-1H-imidazol-2-ylthio)alkanoic acids 28a and 28b, 3-(2,6-dimethylphenoxy)

propanoic acid 25c, and 3-(2,6-dimethylphenoxy)acrylic acid 30a and before incubation under HR conditions. Note that with this protocol, it was necessary to isolate the cells by centrifugation (2 minutes at 31×g) to change buffers; hence, the added compounds were not present during incubation under hypoxic conditions.

Statistical Analyses.

Data were analyzed with GraphPad Prism 5 (GraphPad Software, Inc., La Jolla, Calif.). Data are shown as means±S.D. A value of p<0.05 was used for the rejection of the null hypothesis.

Results.

The phenolic substituents on ω-(phenoxy)alkanoic acids, i.e., 2-methylphenol, 2,6-dimethylphenol, 3,5-dimethylphenol, and 2,6-diisopropylphenol, were chosen because of their antioxidant activity and because the compounds afforded insight into the substrate selectivity of the (β-oxidation pathway (Wright, et al. (2001) *J. Am. Chem. Soc.* 123:1173; Rigobello, et al. (2004) *Free Radic. Res.* 38:315; Ogata, et al. (2005) *Chem. Pharm. Bull.* 53:344; Nantasenamat, et al. (2008) *J. Mol. Graph. Model.* 27:188). Finally, methimazole is an antioxidant and cytoprotective agent (Sausen, et al. (1992) *J. Pharmacol. Exp. Ther.* 260:393; Kim, et al. (2001) *Mol. Pharmacol.* 60:972), and the methimazole prodrugs ω-(1-methyl-1H-imidazol-2-ylthio)alkanoic acids 28a and 28b were investigated as substrates and as cardioprotective agents.

The data presented herein show that ω-(phenoxy)alkanoic acids are substrates for mitochondrial β-oxidation, but that the rates of biotransformation differ markedly depending on the structure. All 3-(phenoxy)propanoic acids and 5-(phenoxy)pentanoic acids studied were biotransformed to phenolic products in isolated rat liver mitochondria (Table 2), but the rates of biotransformation differed markedly.

TABLE 2

| Compound | Rate |
| --- | --- |
| 25a | 2.06 ± 0.50 |
| 25b | 0.39 ± 0.12 |
| 25c | 0.07 ± 0.02 |
| 25d | 0.10 ± 0.06 |
| 26a | 1.27 ± 0.37 |
| 26b | 0.39 ± 0.12 |
| 26c | 0.06 ± 0.01 |
| 26d | 0.01 ± 0.06 |
| 27 | 1.54 ± 0.17 |
| 28a | 2.50 ± 0.31 |
| 28b | 0.97 ± 0.16 |
| 29 | 0.54 ± 0.06 |
| 30a | 1.55 ± 0.14 |
| 30b | N.D. |
| Octanoic acid | 40.3 ± 6.7 |

Rates are expressed as nmol min$^{-1}$ mg protein$^{-1}$. Data are shown as mean±S.D., n=≧3. Statistical analysis (unpaired t-test): 25a vs. 26a, p<0.05; 25b vs. 26b, NS; 25c vs. 26c, NS; 25d vs. 26d, p<0.05; 25a vs. 27, p<0.05; 26a vs. 27, p>0.05; 25c vs. 29, p<0.05; 25c vs. 30a, p<0.05; 26c vs. 29, p<0.05; 25a vs. 30a, p<0.05. N.D., not detected.

With 3-(phenoxy)propanoic acids (25a-25d), the rates of biotransformation decreased with number and position of the methyl groups on the phenoxy moiety in the order: 25a>>25b>25d>25c. A similar pattern was observed with 5-(phenoxy)pentanoic acids where the relative rates of biotransformation were 26a>>26b>26c>26d. In general, the rates of biotransformation of 5-(phenoxy)pentanoic acids were lower than those of similarly substituted 3-(phenoxy) propanoic acids, except that the rates of biotransformation of ω-(2-methylphenoxy)alkanoic acids 25b and 26b were similar. The rate of biotransformation of all ω-(phenoxy)alkanoic acids studied was much lower than that of octanoic acid (Table 2).

Rates of biotransformation of ω-(phenoxy)alkanoic acids 25a and 26a decreased with increasing chain length, but this was not observed with ω-(2-methylphenoxy)-[25b vs. 26b], ω-(2,6-dimethylphenoxy)-[25c vs. 26c], or ω-(3,5-dimethylphenoxy)alkanoic acids [25d vs. 26d] (Table 2). The rates of biotransformation of the ω-(2,6-dimethylphenoxy)-[25c and 26c] and ω-(3,5-dimethylphenoxy)alkanoic acids [25d vs. 26d] were low compared with the unsubstituted analogs.

3-(2-Naphthoxy)propanoic acid 27 was biotransformed at a rate slower than that of 3-(phenoxy)propanoic acid 25a but similar to that of the 5-(phenoxy)pentanoic acid 26a (Table 2).

Although the biotransformation of the alkanoic acids was studied in the presence of carnitine, the biotransformation of alkanoic acids 25a and 29 was studied in both the presence and absence of added carnitine, but no significant difference was observed, likely because sufficient carnitine concentrations were present in isolated mitochondria.

The mitochondrial biotransformation of 5-(2,6-dimethylphenoxy)pentanoic acid 26c was accompanied by the formation of the carnitine ester of acid 26c. In addition, acid 26c was biotransformed to the carnitine ester of acid 25c, but 3-(2,6-dimethylphenoxy)propanoic acid 25c itself was not observed. The formation of the product 2,6-dimethylphenol was, however, observed, indicating that acid 26c underwent two cycles of β-oxidation to release product (FIG. 1). This observation differs from the mitochondrial β-oxidation of dietary fatty acids, which apparently proceeds to product formation with no release of intermediates and is attributed to intermediate channeling (Nada, et al. (1995) *J. Biol. Chem.* 270:530; Liang, et al. (2001) *Biochem. Soc. Trans.* 29:279). The formation of carnitine esters has, however, been observed with other xenobiotic alkanoic acids: the mitochondrial β-oxidation of elaidic acid (9-trans-octadecenoic acid) is accompanied by the formation of 5-trans-tetradecenoylcarnitine (Yu, et al. (2004) *J. Biol. Chem.* 279:52160). The formation of the 5-trans-tetradecenoylcarnitine is attributed to the low rate of dehydrogenation of 5-trans-tetradecanoyl-CoA by the acyl-CoA dehydrogenases, which results in the accumulation of the CoA thioester; the accumulated CoA thioester is converted to the carnitine ester by carnitine palmitoyltransferase-II. Indeed, carnitine ester formation is favored over hydrolysis to the acid (Yu, et al. (2004) supra). ω-(2,6-Dimethylphenoxy)alkanoic acids 25c and 26c were poor substrates for β-oxidation (Table 2). Hence, the observed accumulation of ω-(2,6-dimethylphenoxy)alkanoyl-CoA esters may have been accompanied by the carnitine palmitoyltransferase-II-catalyzed conversion to the corresponding carnitine esters.

5-(Phenoxy)pentanoic acids must undergo two cycles of β-oxidation to release a phenolic metabolite, whereas β-(phenoxy)propanoic acids release a phenolic metabolite after one cycle of β-oxidation (FIG. 1). Moreover, 4-thiaalkanoic acids are better substrates for the medium-chain acyl-CoA dehydrogenase than 4-oxaalkanoic acids (Lau, et al. (1988) *Biochemistry* 27:5089). Hence, 3-([2,6-dimethylphenoxy]methylthio)propanoic acid 29 was prepared to test the hypothesis that the insertion of a methylthio linking group between the 2,6-dimethylphenoxy group and the propanoic acid moiety would result in less steric interaction between the substrate and β-oxidation enzymes and, thereby, increase the rate of biotransformation. The intermediate (2,6-dimethylphenoxy)methanethiol formed from acid 29 after one cycle of β-oxidation would be expected to eliminate thioformaldehyde to afford 2,6-dimethylphenol. Indeed, 4-thiaalkanoic acid 29 proved to be a much better substrate for β-oxidation than ω-(2,6-dimethylphenoxy)alkanoic acids 25c and 26c (Table 2), affording a several-fold increase in reaction rate.

The mitochondrial biotransformation of endobiotic and xenobiotic alkanoic acids requires the medium-chain acyl-CoA dehydrogenase-catalyzed formation of enoyl-CoA intermediates. (E)-3-(2,6-Dimethylphenoxy)acrylic acid 30a was prepared to determine whether circumventing the potential barrier formed by the medium-chain acyl-CoA dehydrogenase might overcome the apparent steric impediment to biotransformation observed with ω-(2,6-dimethylphenoxy) alkanoic acids 25c and 26c (Table 2). The rate of biotransformation of (E)-3-(2,6-dimethylphenoxy)acrylic acid 30a was approximately 20-fold greater than that of the saturated analog 3-(2,6-dimethylphenoxy)propanoic acid 25c, indicating that steric effects play a larger role for the medium-chain acyl-CoA dehydrogenase than for enoyl-CoA hydratase (Table 2). Moreover, no biotransformation of (Z)-3-(2,6-dimethylphenoxy)acrylic acid was detected, which is consistent with the known selectivity of enoyl-CoA hydratase that catalyzes the conversion of (E)-2-alkenoyl-CoA thioesters, but not (Z)-2-alkenoyl-CoA thioesters, to 3-hydroxyalkanoyl-CoA thioesters (Wu, et al. (2000) J. Am. Chem. Soc. 122: 3987). No quantifiable biotransformation was observed with the bulky analog (E)-3-(2,6-diisopropylphenoxy)acrylic acid 30b (Table 2), indicating that steric factors also affect enoyl-CoA hydratase-catalyzed reactions. This is the first demonstration of the utility of using ω-(phenoxy)acrylic acids as prodrugs for antioxidant delivery to mitochondria.

Depolarization of the mitochondrial membrane potential with carbonylcyanide-4-(trifluoromethoxy)phenylhydrazone (FCCP) significantly decreased the biotransformation of ω-(phenoxy)alkanoic acids 25a and 26a (25a: 1.69±0.19, 25a+ FCCP: 0.41±0.12, p<0.05; 26a: 1.17±0.27, 26a+FCCP: 0.64±0.10, p<0.05; rates are expressed as nmol product min$^{-1}$ mg protein$^{-1}$ and are shown as mean±S.D., n=3). The mechanism by which FCCP decreased the biotransformation of ω-(phenoxy)alkanoic acids was not investigated, but may be similar to that of Arochlor 1254, which, like FCCP (Benz & McLaughlin (1983) Biophys. J. 41:381), decreases both the mitochondrial membrane potential and the β-oxidation of palmitate (Aly & Domenech (2009) Toxicology 262:175). The effect of Arochlor 1254 on β-oxidation was attributed to Arochlor 1254-induced impairment of the electron transport chain (Latipáá, et al. (1986) Biochim. Biophys. Acta 875: 293). Several compounds, including perhexyline, amiodarone, benzarone, and benzbromarone, also inhibit mitochondrial β-oxidation (Deschamps, et al. (1994) Hepatology 19:948; Kaufmann, et al. (2005) Hepatology 41:925), but the mechanism by which these drugs inhibit β-oxidation has not been elucidated. Although FCCP may perturb the function of the carnitine shuttle and, hence, the uptake of xenobiotic alkanoic acids by mitochondria, the effect of FCCP on the carnitine shuttle has apparently not been reported. The decreased mitochondrial membrane potential that may accompany pathological mitochondrial dysfunction may, however, reduce the rate of biotransformation of alkanoic-acid-based antioxidant prodrugs.

Figure 2:
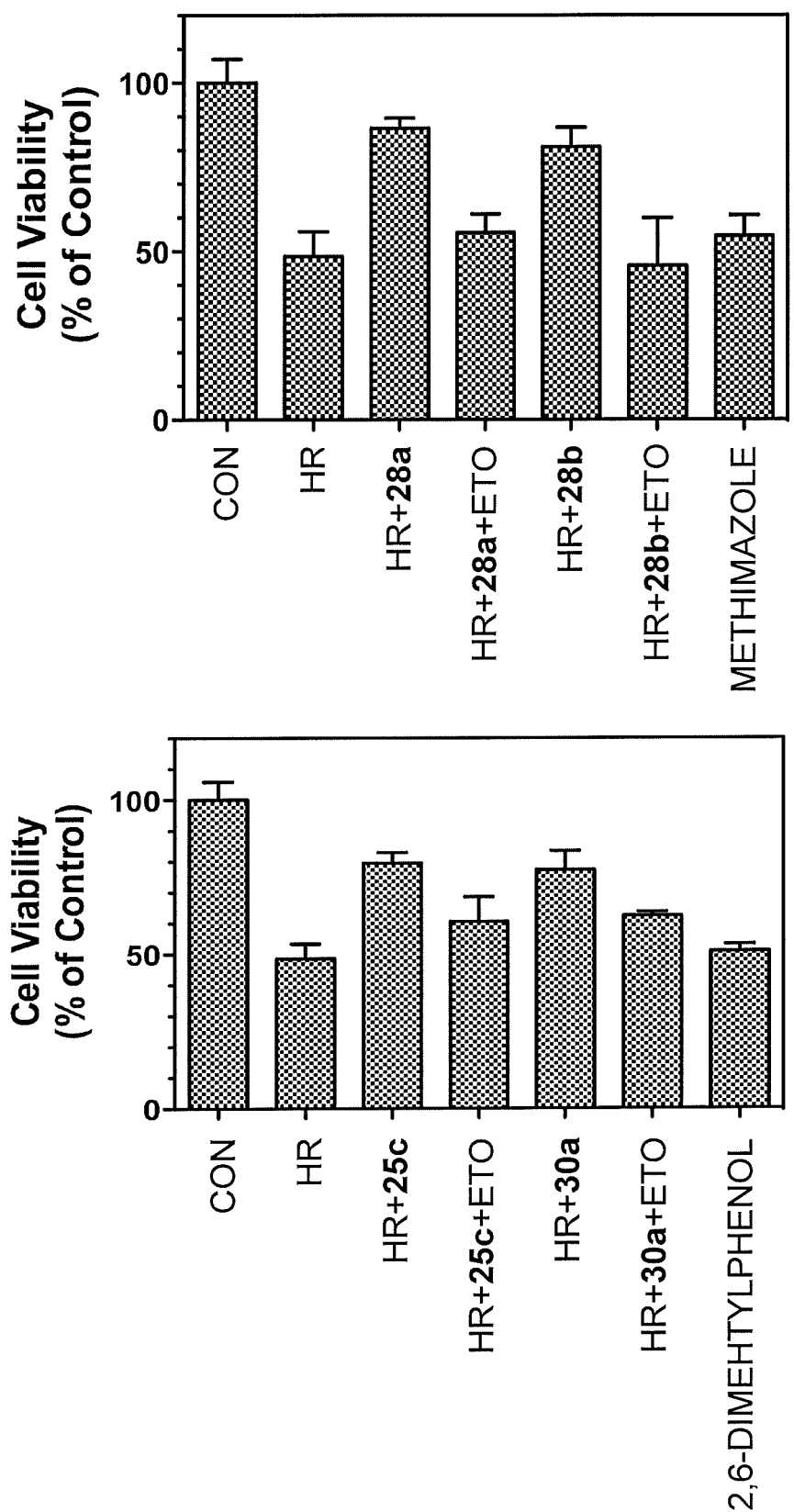
FIG. 2 shows the cytoprotective effects of ω-(1-methyl-1H-imidazol-2-ylthio)alkanoic acids 28a or 28b and 3-(2,6-dimethylphenoxy)propanoic acid 25c and 3-(2,6-dimethylphenoxy)acrylic acid 30a in isolated rat cardiomyocytes. Upper panel: Alkanoic acids 28a and 28b (1 µM), methimazole (1 µM), and etomoxir (20 µM) were incubated with cardiomyocytes in a hypoxia-reoxygenation protocol. CON, control; HR, hypoxia-reoxygenation; Eto, etomoxir. Statistical analysis (one-way ANOVA, n=3): CON vs. HR, $p<0.05$; HR vs. HR+28a, $p<0.05$; CON vs. HR+28a, NS; HR+28a vs. HR+28a+Eto, $p<0.05$; HR vs. HR+28b, $p<0.05$; HR+28b vs. HR+28b+Eto, $p<0.05$; HR vs. Methimazole, NS. Lower panel: Alkanoic acids 25c and 30a (1 µM), 2,6-dimethylphenol (1 µM), and etomoxir (20 µM) were incubated with cardiomyocytes in a hypoxia-reoxygenation protocol. CON, control; HR, hypoxia-reoxygenation; Eto, etoximir. Statistical analysis (one-way ANOVA, n=3): CON vs. HR, $p<0.05$; HR vs. HR+25c, $p<0.05$; CON vs. HR+25c, $p<0.05$; HR+25c vs. HR+25c+Eto, $p<0.05$; HR vs. HR+30a, $p<0.05$; HR+30a vs. HR+30a+Eto, $p<0.05$; HR vs. 2,6-Dimethylphenol, NS.

The cytoprotective potential of the thiol-based antioxidant prodrugs 28a and 28b and of 2,6-dimethylphenol prodrugs 25c and 30a was tested in a hypoxia-reoxygenation protocol with isolated cardiomyocytes, which is a model system relevant to ischemia/reperfusion injury. Incubation of cardiomyocytes with either ω-(1-methyl-1H-imidazol-2-ylthio) alkanoic acids 28a or 28b conferred significant cytoprotection in cardiomyocytes incubated in a hypoxia-reoxygenation protocol (FIG. 2). The cytoprotective effect of ω-(1-methyl-1H-imidazol-2-ylthio)alkanoic acids 28a or 28b was blocked by etomoxir, which inhibits carnitine palmitoyl transferase-I and, thereby, prevents their delivery to mitochondria (Declercq, et al. (1987) J. Biol. Chem. 262:9812). Incubation of cardiomyocytes under the hypoxia-reoxygenation protocol with etomoxir alone exerted no cytoprotective effect. Significantly, incubation of cardiomyocytes under the hypoxia-reoxygenation protocol with methimazole alone failed to provide cytoprotection. Hence, the methimazole prodrugs ω-(1-methyl-1H-imidazol-2-ylthio)alkanoic acids 28a or 28b allow the delivery and release of methimazole to mitochondria and provide cytoprotection that is superior to that afforded by the methimazole itself.

Similarly, both 3-(2,6-dimethylphenoxy)propanoic acid 25c and 3-(2,6-dimethylphenoxy)acrylic acid 30a were cytoprotective in a hypoxia-reoxygenation protocol, and the cytoprotective effects were blocked by etomoxir (FIG. 2).

The observed cytoprotective effects of prodrugs 25c, 28a, 28b, and 30a were likely attributed to their antioxidant actions. Cardiac ischemia/reperfusion injury is characterized by the formation of reactive oxygen species, including superoxide, hydrogen peroxide, and oxygen- and carbon-centered free radicals (Zweier, et al. (1987) Proc. Natl. Acad. Sci. USA 84:1404; Tompkins, et al. (2006) Biochim. Biophys. Acta 1762:223; Lambert, & Brand (2009) In: Methods in Molecular Biology, Walker (Ed.) Humana Press: New York, pp. 165). Accordingly, mitochondrial-targeted antioxidants are of use the management of cardiac ischemia/reperfusion injury. A range of phenols, particularly ortho-substituted phenols, are chain-breaking antioxidants that react with a range of free-radical species (Howard, et al. (1963) Can. J. Chem. 41:2800). 2,6-Dimethylphenol, which is released from prodrugs 25c and 30a, is a chain-breaking antioxidant. Methimazole, which is released from prodrugs 28a and 28b, scavenges superoxide, hydrogen peroxide, hydroxyl radical, and free radicals (Taylor, et al. (1984) FEBS Lett. 176:337; Petry & Eling (1987) J. Biol. Chem. 262:14112; Lagorce, et al. (1997) Pharmacology 55:173). Hence, the cytoprotective actions of prodrugs 25c, 28a, 28b, and 30a are consistent with the pathophysiology of ischemia/reperfusion injury and with the known antioxidant chemistry of 2,6-dimethylphenol and methimazole.

Example 6

Monitoring Mitochondrial Uptake

Renal organic cation transport has been analyzed using [2-(4-Nitro-2,1,3-benzoxadiazol-7-yl)aminoethyl]trimethylammonium 31 (Bednarczyk, et al. (2000) Pflügers Arch. 440:184-192). NBD-TMA is fluorescent, which allows measurement of the activity of transport systems in real-time. The fluorescent properties of nitrobenzofurazan (NBF) is useful for studying mitochondrial uptake of compounds disclosed herein in real-time. Although NBD-TMA itself is transported into mitochondria (it is similar to choline esters), modification of the NBF nucleus allows the study of transport of a range of compounds.

29

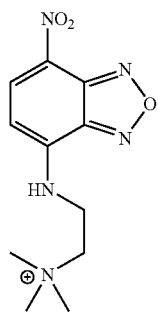

The choline ester of 7-carboxy-4-nitrobenzofurazan 32 allows investigation of uptake. Comparison of triphenylphosphonium-NBD 33 and trimethylammonium-NBD 34 allows comparison of the uptake of a hydrophilic and hydrophobic charged compound.

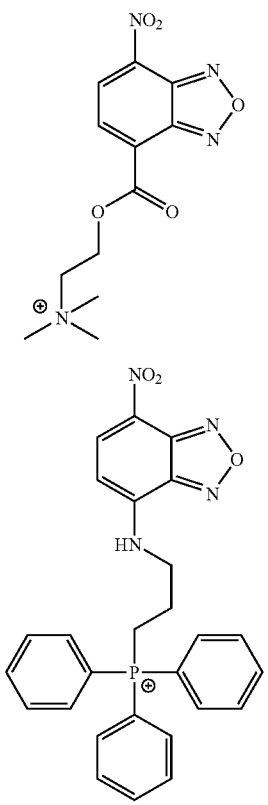

30

-continued

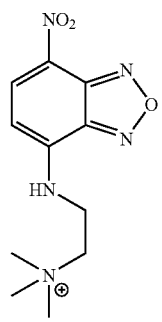

Several compounds can be prepared from the commercially available 4-chloro-7-nitrobenzofurazan. 4-Carboxy-7-nitrobenzofurazan (CAS 32863-22-2) has also been prepared (Dal Mone, et al. (1970) *Annal. Chim.* 60:801-814) and can be used for prepare the choline ester 32. 4-Hydroxy-7-nitrobenzofurazan (CAS 22250-54-0) has been prepared (Uchiyama, et al. (1998) *J. Chem. Soc., Perkin Trans.* 2, 2165-2174) and can also be used to prepare compounds. The fluorescent properties of a range of 4-substituted 7-nitrobenzofurazans has been investigated (Uchiyama, et al. (1998) supra).

What is claimed is:

1. A mitochondria-targeted antioxidant prodrug, wherein said prodrug is a ω-(1-methyl-1H-imidazol-2-ylthio)acrylic acid, a ω-(1,5-dimethylimidazol-4-ylthio)alkanoic acid, or a ω-(1,5-dimethylimidazol-4-ylthio)acrylic acid.

2. A mitochondria-targeted antioxidant prodrug, wherein said prodrug is selected from the group of 3-(2,2,5,7,8-pentamethylchroman-6-yl)pentanoic acid; 3-(1,5-dimethyl-1H-imidazole-4-ylthio)propanoic acid; 3-([2,6-dimethylphenoxy]methylthio)propanoic acid; (E)-3-(2,6-dimethylphenoxy) acrylic acid; and (E)-3-(2,6-diisopropylphenoxy)acrylic acid.

3. A pharmaceutical composition comprising a mitochondria-targeted antioxidant prodrug in admixture with a pharmaceutically acceptable carrier, wherein said prodrug is a 3-(phenoxy)acrylic acid, a ω-(1-methyl-1H-imidazol-2-ylthio)acrylic acid, a ω-(1,5-dimethylimidazol-4-ylthio)alkanoic acid, or a ω-(1,5-dimethylimidazol-4-ylthio)acrylic acid.

4. A pharmaceutical composition comprising a mitochondria-targeted antioxidant prodrug in admixture with a pharmaceutically acceptable carrier, wherein the prodrug is 3-(2,2,5,7,8-pentamethylchroman-6-yl)pentanoic acid; 3-(1,5-dimethyl-1H-imidazol-4-ythio)propanoic acid; 2-(1,3-dithiolan-2-yl)acetic acid; 2-(1,3-dithian-2-yl)acetic acid; 5-(2-methylphenoxy)pentanoic acid; 5-(2,6-dimethylphenoxy)pentanoic acid; 5-(3,5-dimethylphenoxy)pentanoic acid; 3-([2,6-dimethylphenoxy]methylthio)propanoic acid; (E)-3-(2,6-dimethylphenoxy)acrylic acid; or (E)-3-(2,6-diisopropylphenoxy)acrylic acid.

* * * * *